United States Patent
Smith et al.

(10) Patent No.: US 8,391,990 B2
(45) Date of Patent: Mar. 5, 2013

(54) MODULAR ANTITACHYARRHYTHMIA THERAPY SYSTEM

(75) Inventors: Joseph M. Smith, North Oaks, MN (US); Richard Milon Dujmovic, Jr., Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1992 days.

(21) Appl. No.: 11/131,583

(22) Filed: May 18, 2005

(65) Prior Publication Data

US 2006/0265018 A1  Nov. 23, 2006

(51) Int. Cl.
*A61N 1/00* (2006.01)

(52) U.S. Cl. .................. 607/60; 607/4; 607/32

(58) Field of Classification Search ............. 607/4, 32, 607/60
See application file for complete search history.

(56) References Cited

U.S. PATENT DOCUMENTS

| | | | |
|---|---|---|---|
| 4,635,639 A | 1/1987 | Hakala et al. | |
| 4,886,064 A | 12/1989 | Strandberg | |
| 5,078,134 A | 1/1992 | Heilman et al. | |
| 5,383,915 A | 1/1995 | Adams | |
| 5,411,535 A | 5/1995 | Fujii et al. | |
| 5,456,691 A * | 10/1995 | Snell | 607/30 |
| 6,141,588 A * | 10/2000 | Cox et al. | 607/9 |
| 6,272,377 B1 * | 8/2001 | Sweeney et al. | 600/515 |
| 6,351,669 B1 * | 2/2002 | Hartley et al. | 607/5 |
| 6,400,982 B2 * | 6/2002 | Sweeney et al. | 600/515 |
| 6,480,745 B2 | 11/2002 | Nelson et al. | |
| 6,647,292 B1 | 11/2003 | Bardy et al. | |
| 6,721,597 B1 | 4/2004 | Bardy et al. | |
| 6,778,860 B2 | 8/2004 | Ostroff et al. | |
| 6,788,974 B2 | 9/2004 | Bardy et al. | |
| 6,878,112 B2 * | 4/2005 | Linberg et al. | 600/300 |
| 6,922,592 B2 * | 7/2005 | Thompson et al. | 607/59 |
| 6,931,282 B2 * | 8/2005 | Esler | 607/9 |
| 7,142,912 B2 * | 11/2006 | Wagner et al. | 607/4 |
| 7,289,847 B1 * | 10/2007 | Gill et al. | 607/5 |
| 7,333,853 B2 * | 2/2008 | Mazar et al. | 607/2 |
| 7,336,994 B2 * | 2/2008 | Hettrick et al. | 607/5 |
| 2002/0032470 A1 | 3/2002 | Linberg | |
| 2002/0035376 A1 | 3/2002 | Bardy et al. | |
| 2002/0035377 A1 | 3/2002 | Bardy et al. | |

(Continued)

FOREIGN PATENT DOCUMENTS

| | | |
|---|---|---|
| JP | 2005245215 A | 9/1993 |
| JP | 200051373 A | 2/2000 |

(Continued)

OTHER PUBLICATIONS

"Invitation to Pay Additional Fees and Partial Search Report for Application No. PCT/US2006/018824, date mailed Nov. 15, 2006", 5 Pages.

(Continued)

*Primary Examiner* — Nicole F Lavert
(74) *Attorney, Agent, or Firm* — Schwegman Lundberg & Woessner, P.A.

(57) ABSTRACT

This document discusses, among other things, a modular antitachyarrhythmia therapy system. In an example, a modular antitachyarrhythmia system includes at least two separate modules that coordinate delivery an antitachyarrhythmia therapy, such as a defibrillation therapy. In another example, a modular antitachyarrhythmia therapy system includes a sensing module, an analysis module, and a therapy module.

18 Claims, 17 Drawing Sheets

U.S. PATENT DOCUMENTS

| | | |
|---|---|---|
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0091414 A1 | 7/2002 | Bardy et al. |
| 2002/0095196 A1 | 7/2002 | Linberg |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0193846 A1 | 12/2002 | Pool et al. |
| 2003/0028082 A1 | 2/2003 | Thompson |
| 2003/0041866 A1 | 3/2003 | Linberg et al. |
| 2003/0088278 A1 | 5/2003 | Bardy et al. |
| 2003/0097153 A1 | 5/2003 | Bardy et al. |
| 2003/0144701 A1 | 7/2003 | Mehra et al. |
| 2004/0147969 A1 | 7/2004 | Mann et al. |
| 2004/0172071 A1 | 9/2004 | Bardy et al. |
| 2004/0176817 A1 | 9/2004 | Wahlstrand et al. |
| 2004/0176818 A1 | 9/2004 | Wahlstrand et al. |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220626 A1* | 11/2004 | Wagner ............... 607/4 |
| 2004/0220639 A1 | 11/2004 | Mulligan et al. |
| 2005/0061320 A1 | 3/2005 | Lee et al. |
| 2006/0052829 A1* | 3/2006 | Sun et al. ............ 607/4 |
| 2006/0052830 A1* | 3/2006 | Spinelli et al. ..... 607/4 |
| 2006/0206151 A1* | 9/2006 | Lu ....................... 607/4 |
| 2006/0212079 A1* | 9/2006 | Routh et al. ........ 607/4 |
| 2006/0265018 A1 | 11/2006 | Smith et al. |
| 2008/0004663 A1* | 1/2008 | Jorgenson .......... 607/5 |

FOREIGN PATENT DOCUMENTS

| | | |
|---|---|---|
| JP | 2002502640 A | 1/2002 |
| JP | 2004512105 A | 4/2004 |
| JP | 2005508208 A | 3/2005 |
| WO | WO-9826840 A1 | 6/1998 |
| WO | WO-9939767 A1 | 8/1999 |
| WO | WO-0234330 A2 | 5/2002 |
| WO | WO-02098282 A2 | 12/2002 |
| WO | WO-2005000206 A2 | 1/2005 |
| WO | WO-2005042089 A1 | 5/2005 |
| WO | WO-2006124833 A2 | 11/2006 |

OTHER PUBLICATIONS

"International Search Report and Written Opinion for Application No. PCT/US2006/018824, Mailed Mar. 6, 2007", 14 Pages.

"European Application Serial No. 06759887.0, Office Action mailed May 18, 2009", 2 pgs.

"Japanese Application Serial No. 2008-512423, Office Action mailed Nov. 18, 2011", 7 pgs.

"Japanese Application Serial No. 2008-512423, Office Action mailed Feb. 6, 2012", w/ English Translation, 13 pgs.

"Japanese Application Serial No. 2008-512423, Response filed Dec. 22, 2011 to Office Action mailed Nov. 18, 2011", With English Claims, 10 pgs.

"Japanese Application Serial No. 2008-512423, Office Action mailed May 28, 2012", With English Translation, 9 pgs.

* cited by examiner

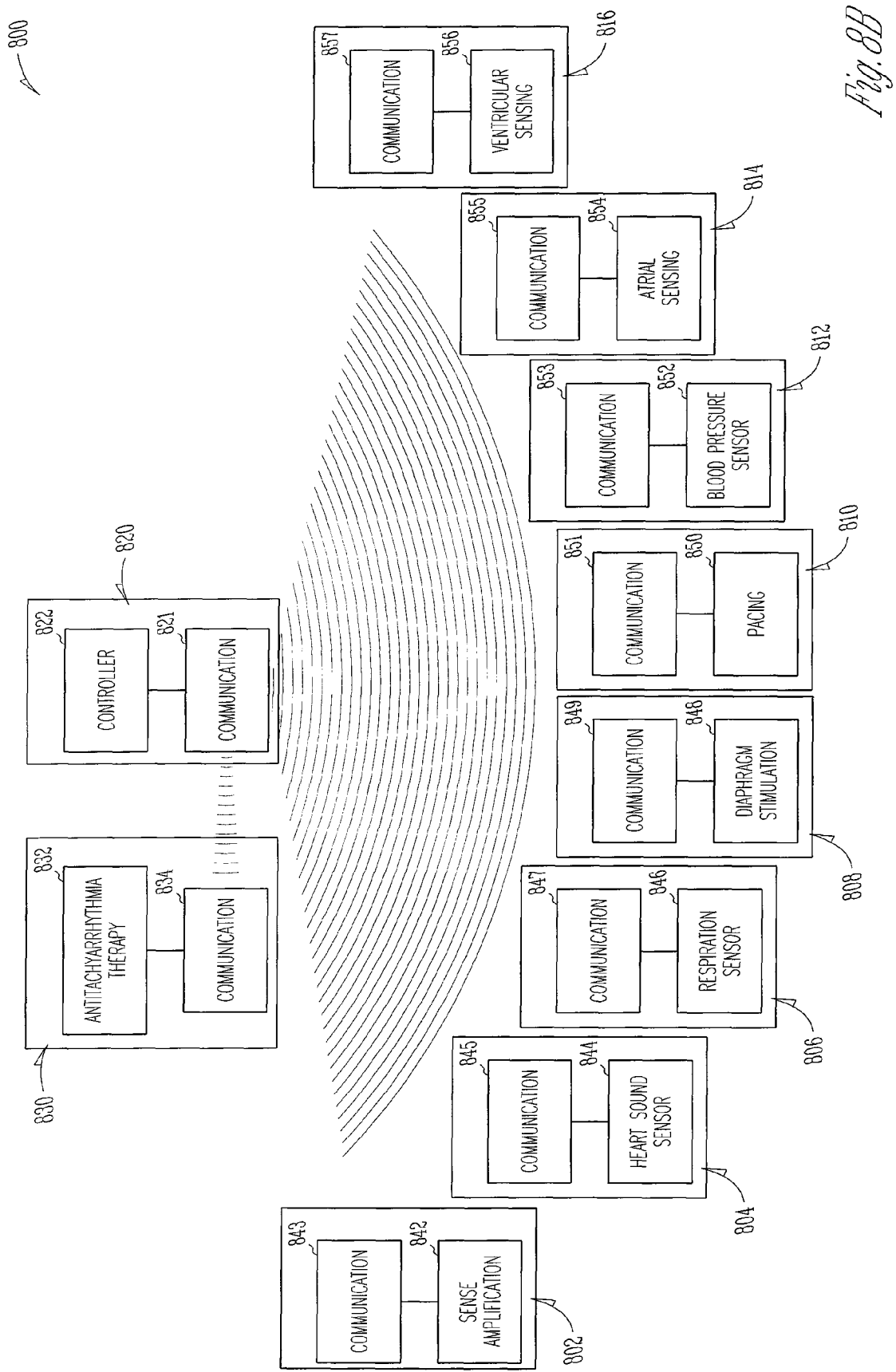

MODULAR ANTITACHYARRHYTHMIA THERAPY SYSTEM

TECHNICAL FIELD

This patent document pertains generally to arrhythmia therapy devices and methods, and more particularly, but not by way of limitation, to modular implantable devices that are configured to deliver an antitachyarrhythmia therapy.

BACKGROUND

Implantable arrhythmia therapy devices such as pacers and defibrillators typically include a power source such as a battery, an electrode, and a controller. A lead carrying the electrode typically has a proximal end that is coupled to a housing that contains the power source and controller, and a distal end that is located in, on, or around the heart. A lead can be introduced into a heart chamber, for example.

A pacing lead typically includes at least one electrode that is configured to deliver a pacing pulse, and a conductor that couples the electrode to a signal generator. Some pacing leads also include a sensing electrode and a second conductor that couples the sensing electrode to a sensing circuit.

A defibrillation lead typically includes an anode and a cathode. For example, a typical defibrillation lead includes two coils that are coupled to anode and cathode portions of a battery. A vector is defined between the anode and cathode. The effectiveness of a defibrillation therapy is affected by the configuration of the anode and cathode, and the vector defined by the anode and cathode.

In some patients, the presence of one or more implanted leads restricts on the patient's range of motion. Moreover, in a growing patient, such as a child, the patient may outgrow a lead. In some growing patients, it can be necessary to periodically explant a pacer or defibrillator and replace the device or implant longer or different leads.

Improved implantable arrhythmia therapy devices are needed.

SUMMARY

In an example, a modular implantable device or system includes an implantable first and an implantable second circuit physically separate from the first circuit. The implantable first circuit includes a sensor to sense a physiologic parameter and a wireless transmitter circuit to send a wireless communication that includes information derived from the physiologic parameter. The implantable second circuit includes a wireless receiver circuit to receive the wireless communication and an antitachyarrhythmia therapy circuit to deliver a responsive antitachyarrhythmia therapy.

In another example, a modular implantable device or system includes an implantable first circuit, an implantable second circuit, physically separate from the first circuit, and an implantable third circuit, physically separate from the second circuit. The implantable first circuit includes a sensor to sense a physiologic parameter, and a communication or driver circuit to send a communication that includes information about the physiologic parameter. The implantable second circuit includes a receiver circuit to receive the communication from the first implantable circuit, a controller circuit to analyze the information about the physiologic parameter, and a wireless transmitter circuit to send a wireless therapy instruction. The implantable third circuit includes a wireless receiver to receive the wireless therapy instruction, and an antitachyarrhythmia therapy circuit to deliver an antitachyarrhythmia therapy.

In another example, a modular implantable device includes an implantable first defibrillation circuit module configured to deliver a first defibrillation shock, an implantable second defibrillation circuit module, physically separate from the first defibrillation circuit module, configured to deliver a second defibrillation shock concurrent with the first defibrillation shock, and a controller circuit configured to direct coordinated delivery of the first and second defibrillation shocks.

BRIEF DESCRIPTION OF THE DRAWINGS

In the drawings, which are not necessarily drawn to scale, like numerals describe substantially similar components throughout the several views. The drawings illustrate generally, by way of example, but not by way of limitation, various embodiments discussed in the present document.

FIG. 8B is a schematic illustration of the system shown in FIG. 8A.

DETAILED DESCRIPTION

Overview

An antitachyarrhythmia system, such as a defibrillation system, includes at least two physically separate modules that communicate with each other through a wireless communication. Numerous example systems are shown in FIGS. 1A to 8B. A module is a component that is used with other components, from which it is physically separate when implanted in the body. For example, in FIG. 1A, module 105 is used with module 110 and is physically separate from module 110.

Examples of wireless communication techniques include a radio frequency (RF) signal, inductive coupling, or conduction through the body. Wireless communications between modules include, for example, information about or derived from a physiologic parameter detected by a sensor, or one or more instructions to deliver, schedule, synchronize, or coordinate delivery of an antitachyarrhythmia therapy. In one example, wireless communication between modules avoids or reduces the use of leads. In some examples, all of the modules are physically disjoint, i.e. there are not physical connections between them. FIGS. 1A-4A show examples of physically disjoint modules. In other examples, some of the modules are physically disjoint, and others are connected. For example, the systems shown in FIGS. 5A and 6A include at least one leadless module and at least one module coupled to a lead.

In an example, a modular antitachyarrhythmia system permits growth of a patient. For example, a system implanted in a child can expand as a child grows, i.e. the modules can still operate as they become farther apart as the child grows because the modules are not tied together with leads. In another example, a modular antitachyarrhythmia system provides free range of motion to a patient.

Figure 1A:
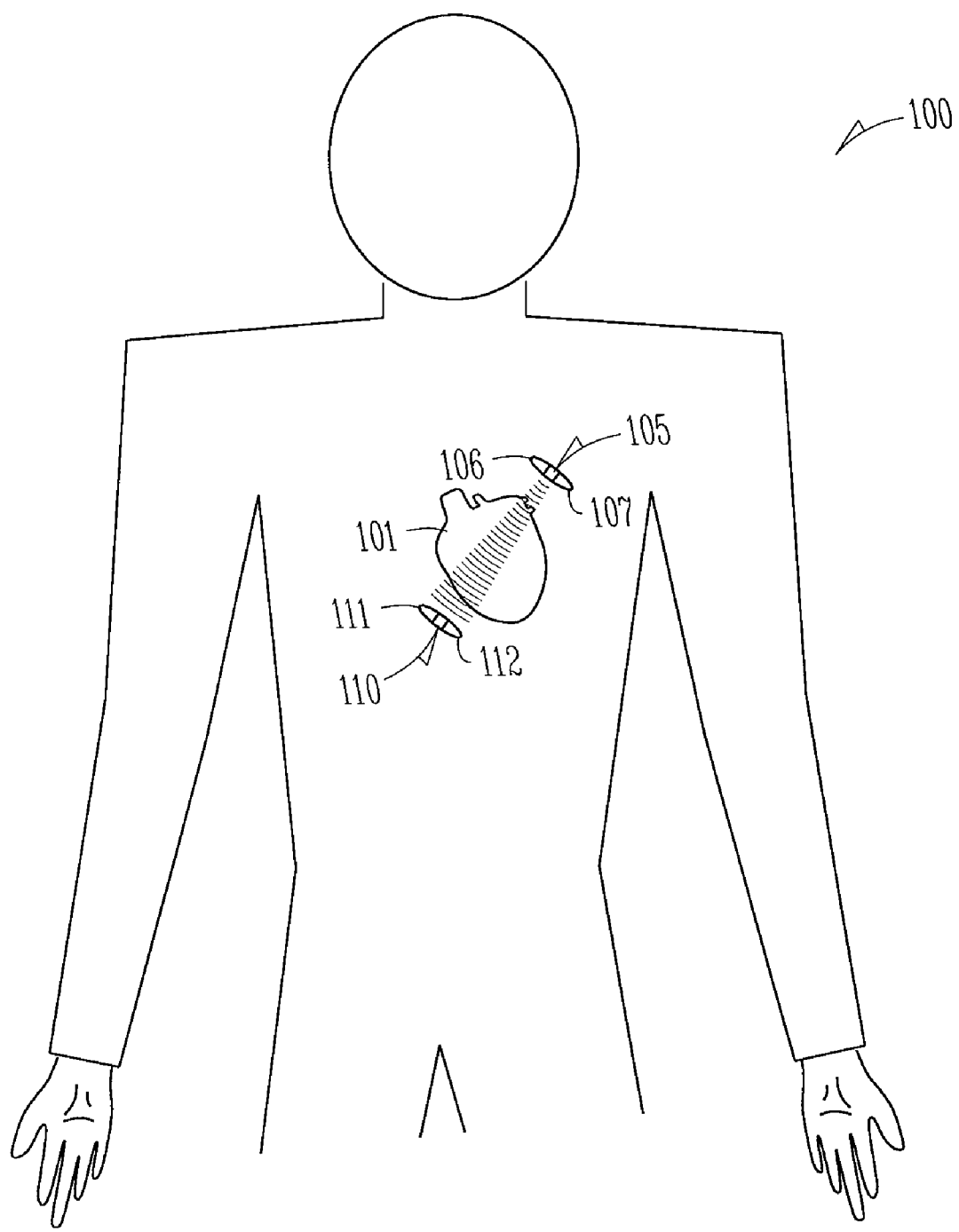
FIG. 1A is an illustration of a modular antitachyarrhythmia system that includes two antitachyarrhythmia therapy modules.

Modular antitachyarrhythmia systems, such as the systems shown in FIGS. 1A-8B, can be used in one or more of a variety of applications. In one example, unique flux fields are created by strategically positioning modules containing electrodes. For example, defibrillation vectors can be tailored by carefully positioning modules. The example illustrated in FIG. 1A shows two separate defibrillation modules implanted near the heart. FIG. 2A shows two separate defibrillation modules implanted in the heart. In some examples, leadless modules with electrodes are implantable in locations that would be practically impossible using tethered systems, such as certain portions of the peripheral vasculature. In an example, a module is sized and shaped for implantation in the pulmonary vasculature, such as in the pulmonary vasculature bed, or in the renal vasculature. In an example, one or more modules is implanted subcutaneously or submuscularly. In an example, a module is sized and shaped for implantation in the intraclavicle space inferior to the clavicle. In another example, a module is sized and shaped for implantation on or around the solar plexus. In another example, a module is sized and shaped for submuscular, intramuscular, intracardiac, or intravascular implantation. In an example, an intravascular or intracardiac module avoids occluding a blood vessel or interfering with valve heart valves.

In an example, modules are implanted in locations that allow for near-field sensing of an intrinsic electrical heart signal. In one example, separate modules are positioned in or around specific locations of the heart or peripheral vasculature so that local intrinsic signals can be sensed at specific locations. In an example, a module is sized and shaped for implantation in a right ventricular apex. In an example, a module is sized and shaped for endocardial implantation, for example in a right atrium or right ventricle. In an example, a module is sized and shaped for implantation in a right atrial appendage. In an example, a module is sized and shaped for implantation in the coronary sinus, in vessels extending from the coronary sinus, or in other venous vasculature. In an example, a module is sized and shaped for implantation on an epicardial surface, such as on a left atrium or left ventricle epicardial surface.

In other examples, a module that is depleted or dysfunctional is replaced, while one or more other modules are left intact. In one example, a module implanted in the heart is left in place, while a module implanted outside the heart is replaced or upgraded. A subcutaneously implanted module, for example, is replaceable with a relatively noninvasive procedure.

Some examples of a modular antitachyarrhythmia system can also be changed over time as needed by replacing or adding one or more modules. For example, analysis or therapy programming circuits can be replaced or upgraded. In another example, pacing capability can be added by adding a pacing module. Modules can be added as a disease progresses or changes.

In another example, a modular antitachyarrhythmia therapy system is implanted in a growing patient, such as a child. In an example, dissemination of the total volume of the modular system over more than one anatomic location enables local organ growth and overall body growth without compromising the functionality of the system. In an example, the reduction or elimination of leads enables organ growth or overall body growth, as the distance between components is allowed to change as the patient grows.

In an example implant method, the components of a system are implanted at predetermined anatomical locations in a patient. In an example, the components are then tested using a standardized protocol. In an example, the standardized protocol is integrated into an external programmer or other adjunct device.

Examples of Modular Antitachyarrhythmia Systems

FIG. 1 is an example of a modular antitachyarrhythmia therapy system 100. In one example, the antitachyarrhythmia system 100 includes two separate antitachyarrhythmia therapy modules 105, 110 that cooperate to deliver a coordinated therapy. Module 105 includes two electrodes 106, 107 and module 110 includes two electrodes 111, 112. In an example, the modules 105, 106 each include a hermetically sealed electronics unit. In an example, the hermetically sealed electronics unit includes a housing and a header, and the electrodes 106, 107, 111, 112 are located on the housing, on the header, or are contained in a lead that is coupled to a module header. In an example, module 105 delivers an antitachyarrhythmia therapy from electrode 106 through a portion of the heart 101 to electrode 107, and module 110 delivers an antitachyarrhythmia therapy from electrode 111 through a portion of the heart 101 to electrode 112. In an example, the modules communicate with each other through wireless communication. In an example, the modules 105, 110 coordinate or synchronize an antitachyarrhythmia therapy through the wireless communication.

In an example, one or both of the modules 105, 110 are implanted in the heart. In another example, one or both of the modules is implanted in the body but outside of the heart. In an example, at least one of the modules is sized and shaped for implantation in a peripheral cardiac vessel, such as the coronary sinus. In an example, a module includes a fixation helix that connects the module to heart tissue.

In an example, a module is sized and shaped to be wedged into a vessel, such as in renal vasculature or pulmonary vasculature. In an example, a module is sized and shaped to be wedged into a vessel having a diameter that decreases in diameter along the length of the vessel, and wedging the module into the vessel fixes the module in place. In an example, the module occludes a portion of venous vasculature.

In another example, a module is sized and shaped for implantation in coronary vasculature, such as in the coronary sinus. In an example, the module is driven in place using a lead.

In an example, the modules 105, 110 shown in FIG. 1A are both fully functional defibrillators, i.e. both modules includes sensing, analysis, and therapy circuitry. In another example, the modules operate in a master/slave relationship. In one example, module 105 operates as a master and includes analysis circuitry that directs delivery of an antitachyarrhythmia therapy through electrodes 111, 112, in module 110.

Figure 1B:
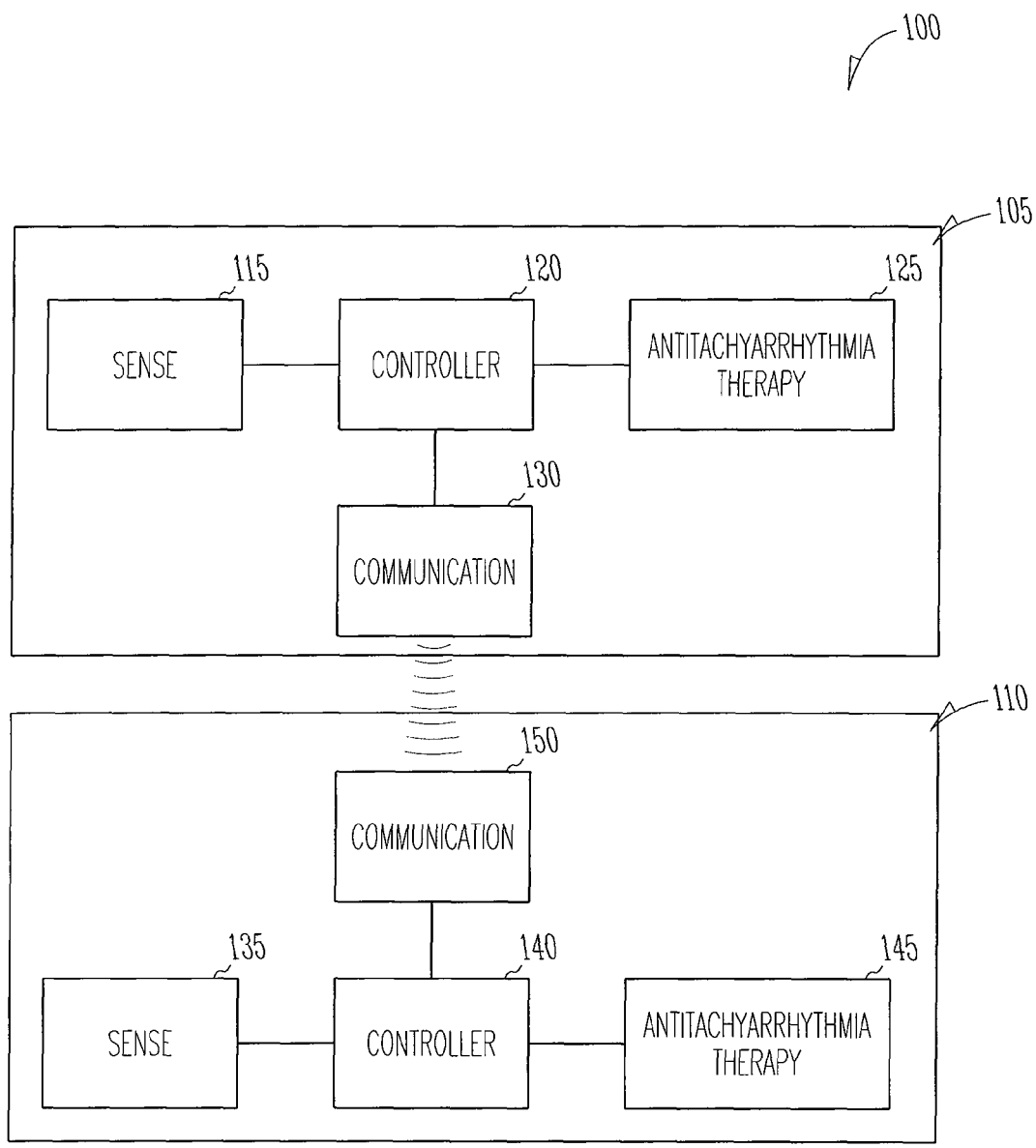
FIG. 1B is a schematic illustration of the system shown in FIG. 1A.

FIG. 1B shows a schematic illustration of one example of the system illustrated in FIG. 1A. In this example, module 105 includes sense circuit 115, controller circuit 120, antitachyarrhythmia therapy circuit 125, and communication circuit 130. In an example, the communication circuit 130 includes telemetry circuitry, such as an RF or inductive transceiver. In another example, the communication circuit uses a human or animal body as a conductive medium for a wireless communication. Sense circuit 115 detects one or more physiological parameters, such as cardiac performance data. In an example, sense circuit 115 includes a sense amplification circuit to detect at least one intrinsic electrical heart signal. Controller circuit 120 analyzes physiological data detected by the sense circuit 115, determines whether a tachyarrhythmia is present, and determines at least one responsive antitachyarrhythmia therapy, such as a defibrillation shock therapy or antitachyarrhythmia pacing therapy. Antitachyarrhythmia therapy circuit 125 delivers the antitachyarrhythmia therapy determined by the controller circuit 120. Antitachyarrhythmia circuit 125 includes the electrodes 106, 107 shown in FIG. 1A. In an example, the antitachyarrhythmia circuit includes a pulse generator coupled to the electrodes, as shown in FIG. 9A. In an example, the pulse generator includes a battery, a capacitor, and circuitry for charging the capacitor and delivering a defibrillation therapy.

In an example, module 110 is a second fully function defibrillator that includes a sense circuit 135, a controller circuit 140, an antitachyarrhythmia therapy circuit 145, and a communication circuit 150. Controller circuit 140 analyzes physiological data detected by the sense circuit 135, determines whether a tachyarrhythmia is present, and determines at lease one responsive antitachyarrhythmia therapy, which is delivered through the antitachyarrhythmia circuit 145. The modules 105, 110 communicate with each other through the communication circuits 130, 150, such as to coordinate, schedule, or synchronize therapy.

In an example master/slave system, one of the modules 105, 110 also determines a therapy to be delivered through one of the modules 105, 110. In an example, module 110 operates as a slave module. In one example, module 110 does not include an analysis circuit. In this example, controller circuit 120 of module 105 determines a therapy based upon data received from sense circuit 135 and directs the antitachyarrhythmia therapy circuit 145 in the other module 110 to deliver a responsive therapy. In another example, module 110 includes neither a sense circuit nor an analysis circuit, and a therapy is determined from data provided by sense circuit 115 in module 105. In another example, module 110 includes an analysis circuit, but module 105 determines an appropriate antitachyarrhythmia therapy and directs delivery of the therapy through module 110.

In an example, a pacing circuit is also provided in one or both of the antitachyarrhythmia modules. In another example, a physically separate pacing module including pacing circuitry and communication circuitry is provided, with the separate pacing module configured for communication with one or both of the modules 105, 110.

In an example, a therapy for a patient is tailored by strategically positioning the antitachyarrhythmia modules 105, 110 in anatomical locations to obtained desired vectors. In an example, the modules are implanted outside the heart, as shown in FIG. 1A. Alternatively, one or both modules are implanted in the heart. In an example, the modules 105, 110 are implantable in a location that can be difficult to reach with an electrode tethered to a lead. In an example, one of the modules 105, 110 is implanted in or on the left side of the heart 101. In an example, a module is sized and shaped for implantation in the coronary sinus, in a vessel extending from the coronary sinus, or on an epicardial or pericardial surface. In an example, a module is affixed using a T-bar and a modified suture technique. In an example, the T-bar has an opening through which a needle is inserted.

The left side of the heart is relatively difficult to reach with an endocardial defibrillation lead because of the complex vasculature through which such a lead would be inserted to reach the left side of the heart. In an example, implantation of a module avoids occlusion of a blood vessel or interference with a heart valve.

Figure 2A:
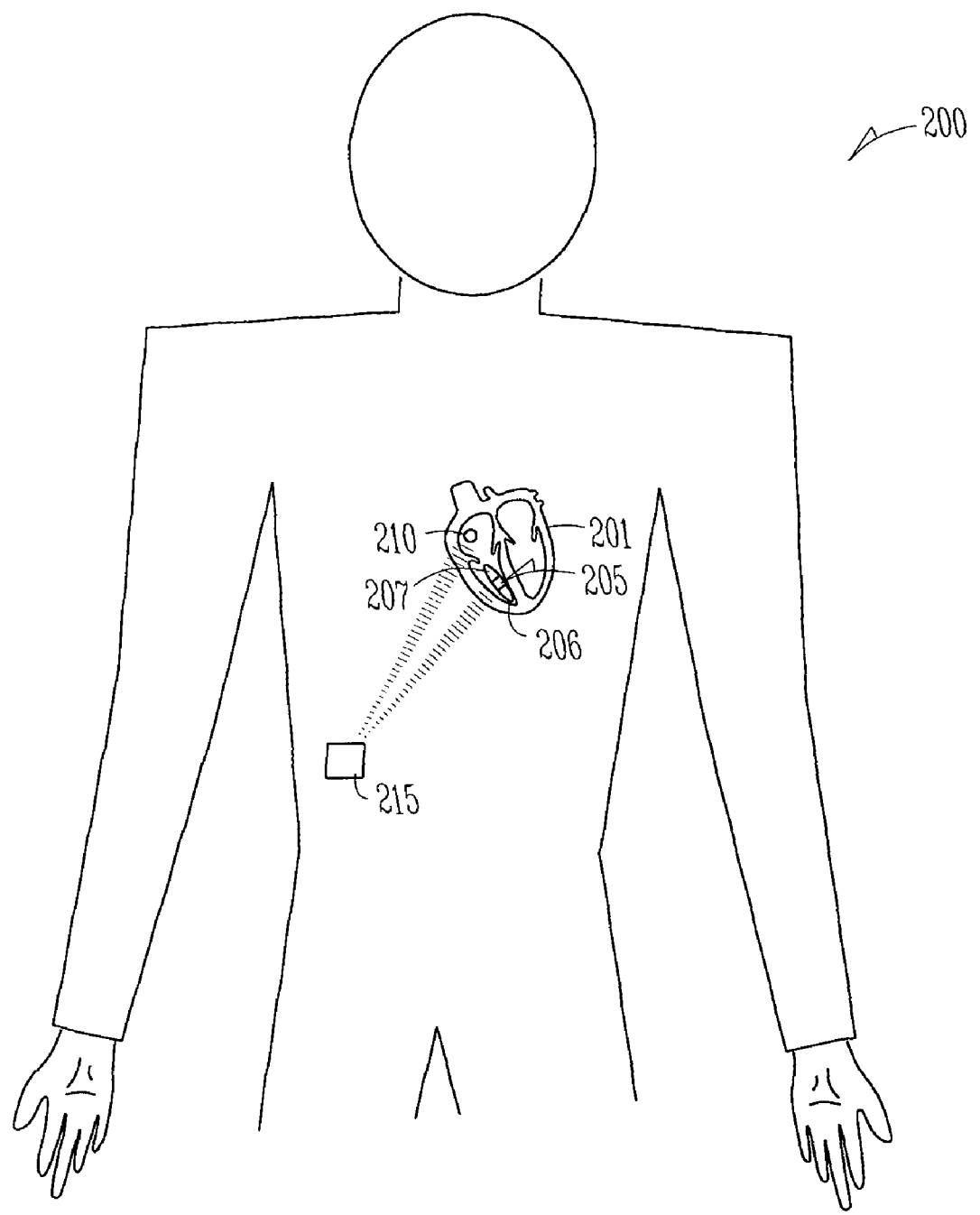
FIG. 2A is an illustration of a modular antitachyarrhythmia system that includes a sensing module, an analysis module, and a therapy module.

Another example of a modular antitachyarrhythmia therapy system is shown in FIG. 2A. The example antitachyarrhythmia system 200 includes three separate modules 205, 210, 215 that respectively perform therapy, sensing, and analysis. Sensing module 210 includes a sensor that detects at least one physiologic parameter, such as an intrinsic electrical heart signal or blood pressure. In another example, sensing module 210 is implanted on or around the heart. Analysis module 215 wirelessly receives information from sensing module 210 and processes the information to determine whether a tachyarrhythmia is present and determine an appropriate antitachyarrhythmia therapy. Analysis module 215 directs therapy module 205 to deliver an antitachyarrhythmia therapy through electrodes 206, 207. In an example, therapy module 205 delivers an antitachyarrhythmia therapy from electrode 206 through a portion of the heart 201 to electrode 207.

Figure 2B:
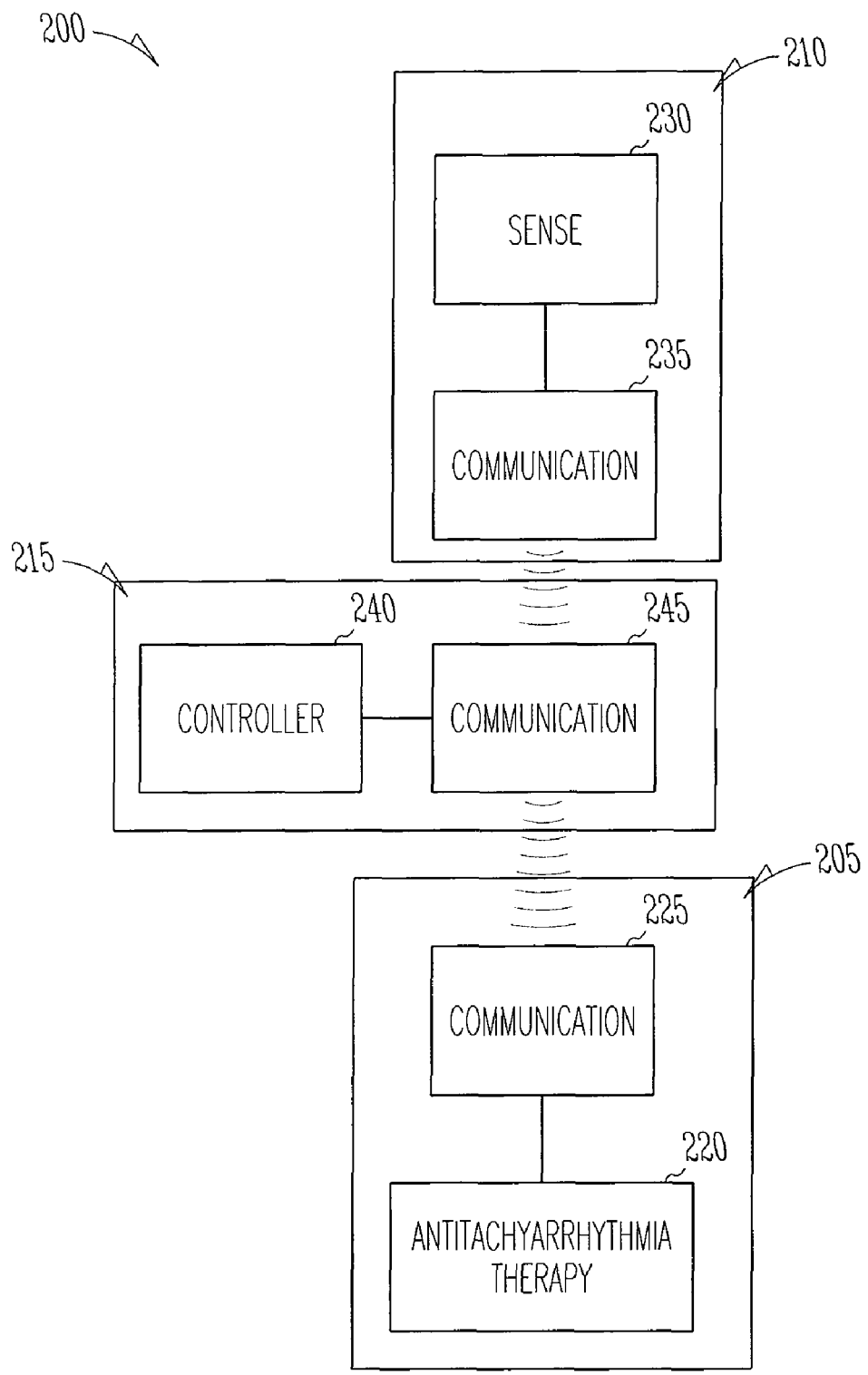
FIG. 2B is a schematic illustration of the system shown in FIG. 2A.

FIG. 2B shows a schematic illustration of the system illustrated in FIG. 2A. In this example, sensing module 210 includes sensor circuit 230, which detects one or more physiological parameters, such as an intrinsic electrical heart signal. Sensing module 210 also includes a communication circuit 235 that wirelessly sends information about the one or more sensed parameters to the analysis module 215. In one example, the communication circuit 235 includes telemetry circuitry, such as an inductive or RF transmitter or transceiver. Analysis module 215 includes controller circuit 240 and a communication circuit 245 that receives information sent by the communication circuit 235 in the sensing module 210. Controller circuit 240 analyzes physiological data provided by the sensing module 210 and determines whether an antitachyarrhythmia is present and, if so, determines an appropriate antitachyarrhythmia therapy, such as a defibrillation shock therapy or antitachyarrhythmia pacing (ATP) therapy. The communication circuit 245 also includes a wireless transmitter, through which a direction is sent to the antitachyarrhythmia therapy module 205 to deliver the antitachyarrhythmia therapy. Antitachyarrhythmia therapy module 205 includes a communication circuit 225 including a wireless receiver that receives the communication from the communication circuit 245 in the analysis module 215. Antitachyarrhythmia therapy module 205 also includes an antitacyarrhythmia therapy circuit 220, which includes or is coupled to the electrodes 206, 207 shown in FIG. 2A. The antitachyarrhythmia therapy circuit 220 delivers the antitachyarrhythmia therapy determined by the controller circuit 240 through the electrodes 206, 207.

In an example, a pacing circuit is also provided in the antitachyarrhythmia module 205, the sensing module 210, or the analysis module 215. In another example, the system includes a separate pacing module including pacing circuitry and communication circuitry.

In an example, a therapy for a patient is obtained by strategically positioning the antitachyarrhythmia therapy module 205 in a particular anatomical location. In an example, the antitachyarrhythmia therapy module 205 is implanted in the heart, as shown in FIG. 2A. In an example, the antitachyarrhythmia therapy module 205 is implanted in the right ventricle. In another example, the module 205 is implantable in or on the left side of the heart. In an example, the sensing module 210 is also placed in a desired location for sensing one or more parameters, such as an intrinsic electrical heart signal. In an example, the analysis module 215 is implanted subcutaneously, which allows the analysis module 215 to be replaced or upgraded without requiring replacement of other separate modules that are implanted deeper in the body. In another example, the analysis module 215 is implanted near the abdomen, as shown in FIG. 2A. Alternatively, the analysis module 215 is implanted subcutaneously, such as on the left side of the upper body near the heart.

Figure 3A:
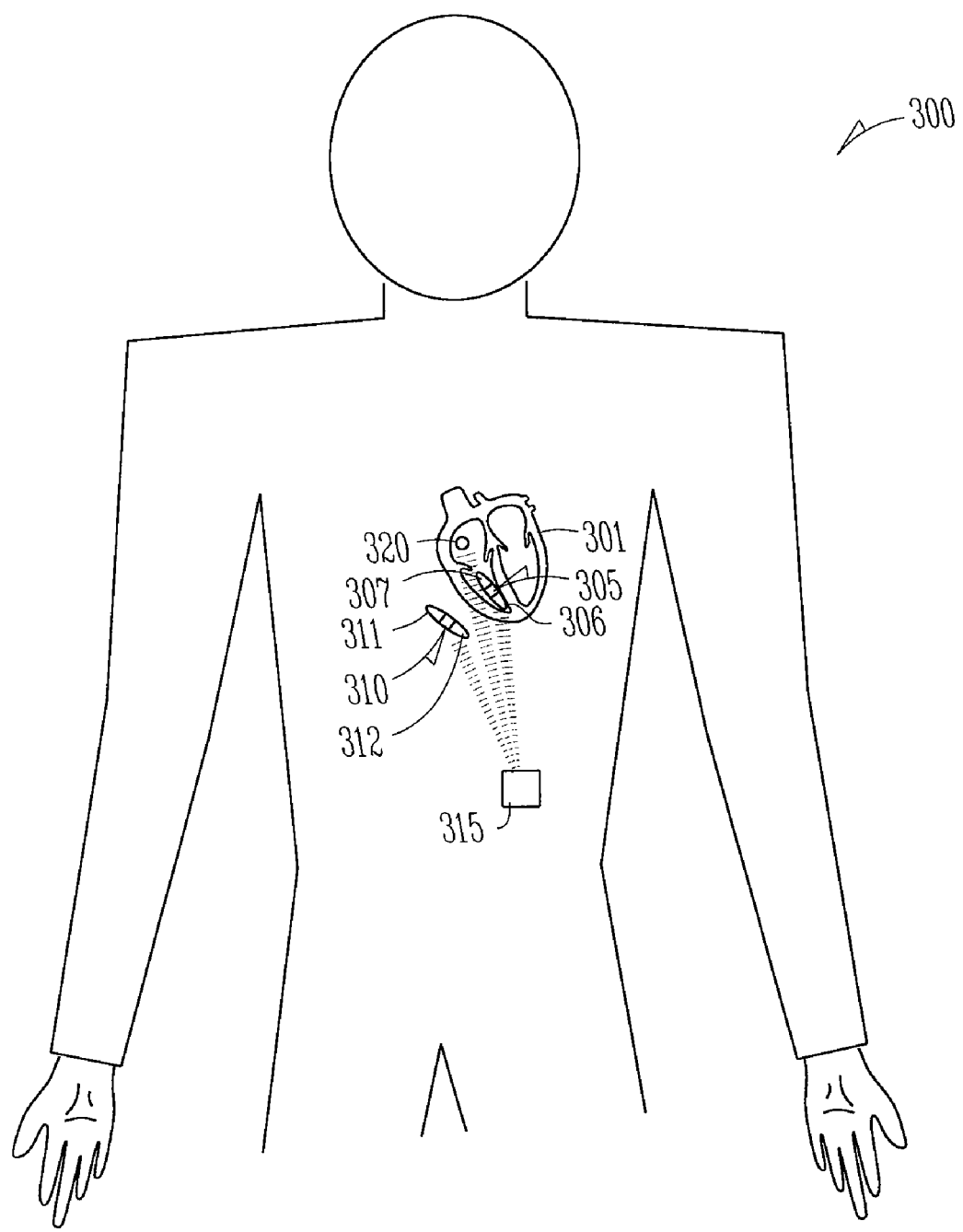
FIG. 3A is an illustration of a modular antitachyarrhythmia system that includes a sensing module, an analysis module, and a two therapy modules.

Another example of a modular antitachyarrhythmia therapy system 300 is shown in FIG. 3A. The example antitachyarrhythmia system 300 includes a sensing module 320, a separate analysis module 315, and two separate antitachyarrhythmia therapy modules 305, 310 that deliver a coordinated antitachyarrhythmia therapy. Sensing module 320 includes a sensor that detects a physiologic parameter, such as an intrinsic electrical heart signal or blood pressure. Analysis module 315 receives information from sensing module 320 and processes the information to determine an antitachyarrhythmia therapy. Analysis module 315 directs therapy modules 305, 310 to deliver a coordinated antitachyarrhythmia therapy through electrodes 306, 307, 311, 312. In an example, therapy module 305 delivers an antitachyarrhythmia therapy from electrode 306 through a portion of the heart 301 to electrode 307, and therapy module 310 delivers an antitachyarrhythmia therapy from electrode 311 through a portion of the heart 301 to electrode 312.

Figure 3B:
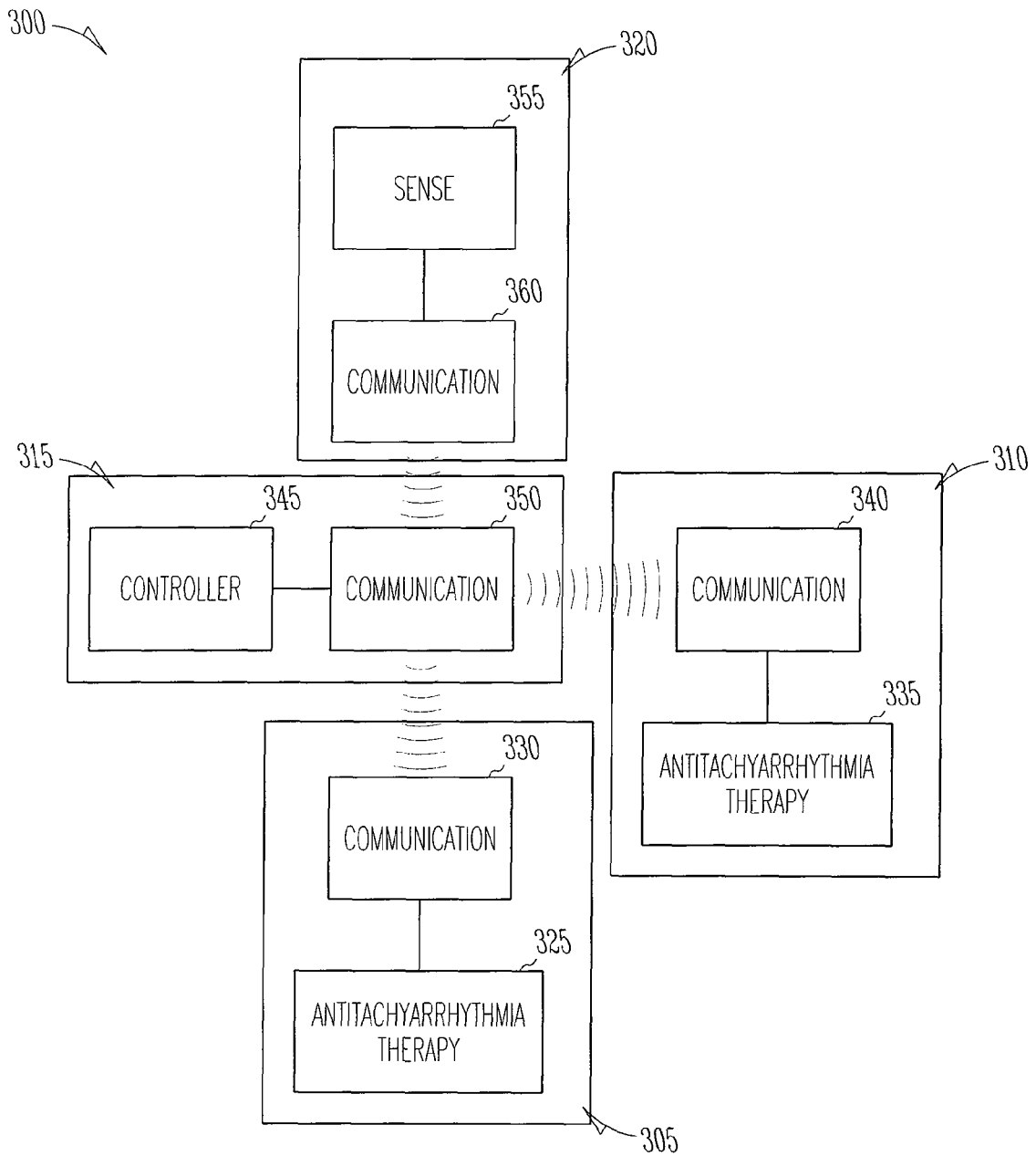
FIG. 3B is a schematic illustration of the system shown in FIG. 3A.

FIG. 3B shows a schematic illustration of the system illustrated in FIG. 3A. Sensing module 320 includes sensor circuit 355, which detects one or more physiological parameters, such as an intrinsic electrical heart signal. Sensing module 320 also includes a communication circuit 360 that sends information about the one or more sensed parameters to the analysis module 315. In one example, the communication circuit 360 in the sensing module 320 includes telemetry circuitry, such as an inductive or RF transmitter. In another example, the communication circuit 360 includes an inductive or RF transceiver. Analysis module 315 includes controller circuit 345 and communication circuit 350. The communication circuit 350 in the analysis module 315 receives information sent by the communication circuit 360 in the sensing module 320. Controller circuit 345 analyzes physiological data provided by the sensing module 320 and determines an antitachyarrhythmia therapy, such as a defibrillation shock therapy. Antitachyarrhythmia therapy modules 305, 310 include respective communication circuits 330, 340 that receive a communication from the communication circuit 350 in the analysis module 315. Antitachyarrhythmia therapy modules 305, 310 also include respective antitachyarrhythmia circuits 325, 335, which respectively include the electrodes 306, 307, 311, 312 shown in FIG. 3A. Antitachyarrhythmia therapy modules 305, 310 deliver the antitachyarrhythmia therapy determined by the controller circuit 345 through the electrodes 306, 307, 311, 312. In an example, the analysis module coordinates delivery of a therapy by the antitachyarrhythmia modules 305, 310. In another example, the communication circuits 330, 340 in the antitachyarrhythmia modules 305, 310 communicate with each other to coordinate or synchronize an antitachyarrhythmia therapy.

In an example, the analysis module 315 is implanted subcutaneously and can be replaced or upgraded with a relatively minor procedure without altering or disturbing the other modules in the system. In an example, antitachyarrhythmia therapy module 305 is implanted in the heart and antitachyarrhythmia therapy module 310 is implanted outside the heart. In another example, antitachyarrhythmia therapy module 305 is implanted in the left side of the heart and antitachyarrhythmia therapy module 310 is implanted in the right side of the heart. In an example, sensing module 320 or other modules are in or on the heart, or in an epicardial space. In an example, sensing module 320 is implanted in the right side of the heart.

Figure 4A:
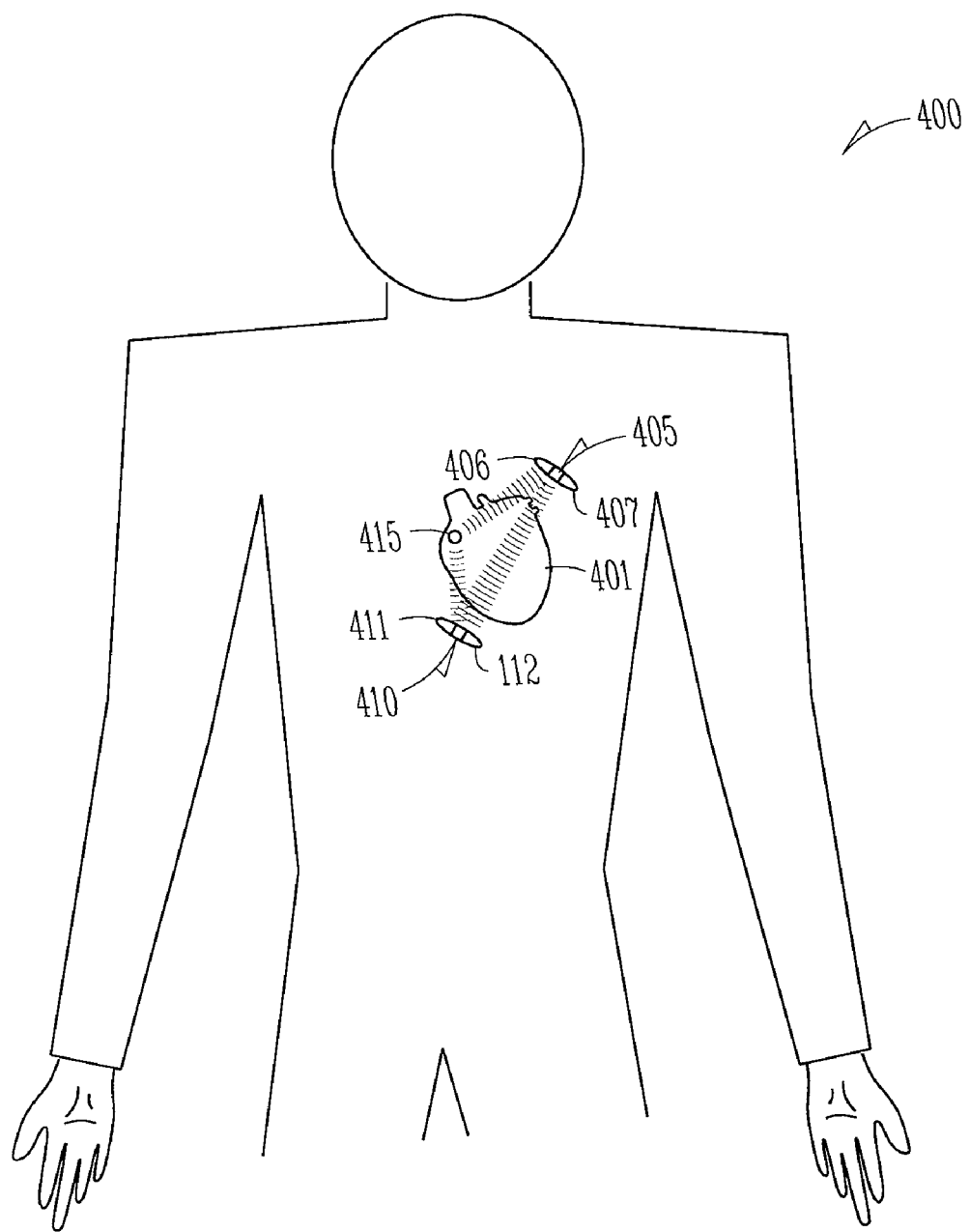
FIG. 4A is an illustration of a modular antitachyarrhythmia system that includes a sensing module and two antitachyarrhythmia therapy modules.

Another example of a modular antitachyarrhythmia therapy system is shown in FIG. 4A. The example antitachyarrhythmia system 400 includes a sensing module 415 and two separate antitachyarrhythmia therapy modules 405, 410. Sensing module 415 includes a sensor that detects a physiologic parameter, such as an intrinsic electrical heart signal or blood pressure. Therapy module 405 includes two electrodes 406, 407 and therapy module 410 includes two electrodes 411, 412. In an example, therapy module 405 delivers an antitachyarrhythmia therapy from electrode 406 through a portion of the heart 401 to electrode 407, and therapy module 410 delivers an antitachyarrhythmia therapy from electrode 411 through a portion of the heart 401 to electrode 412. The modules 405, 410, 415 communicate wirelessly. In an example, the therapy modules 405, 410 coordinate or synchronize a therapy through the wireless communication.

Figure 4B:
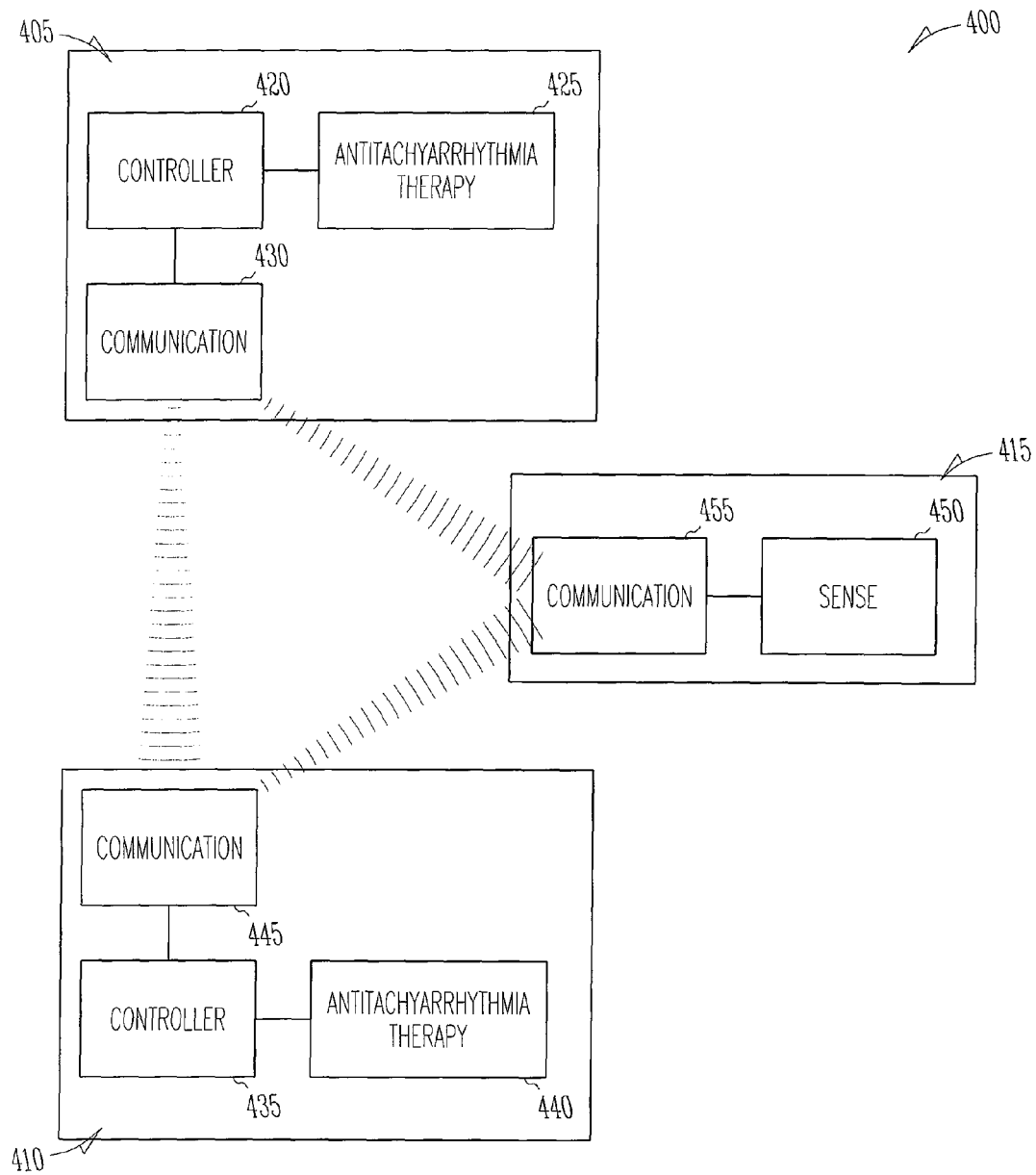
FIG. 4B is a schematic illustration of the system shown in FIG. 4A.

FIG. 4B shows a schematic illustration of the system illustrated in FIG. 4A. Sensing module 415 includes sense circuit 450, which detects one or more physiological parameters, such as an intrinsic electrical heart signal. Sensing module 415 also includes a communication circuit 455 that sends information about the one or more sensed parameters to the other modules. In one example, the communication circuit 455 includes an inductive or RF transmitter. In another example, the communication circuit 455 includes an inductive or RF transceiver. Modules 405, 410 include respective controller circuits 420, 435, antitachyarrhythmia therapy circuits 425, 440 and communication circuits 430, 445. The communication circuits 430, 445 receive information from the communication circuit 455 in the sensing module 415. Controller circuits 420, 435 analyze physiological data provided by the sense circuit 450 and determine an antitachyarrhythmia therapy, such as a defibrillation shock therapy. Antitachyarrhythmia therapy circuits 425, 440 include the respective electrodes 406, 407 and 410, 411. Antitachyarrhythmia therapy circuits 425, 440 deliver an antitachyarrhythmia therapy determined by the respective controller circuit 420, 435 through the respective electrodes 406, 407 and 410, 411. In an example, antitachyarrhythmia modules 405, 410 communicate to coordinate or synchronize delivery of an antitachyarrhythmia therapy.

In an example, separate modules 405, 410, 415 are implanted outside the heart. In another example, one or more of the separate modules 405, 410, 415 are implanted in the heart.

Figure 5A:
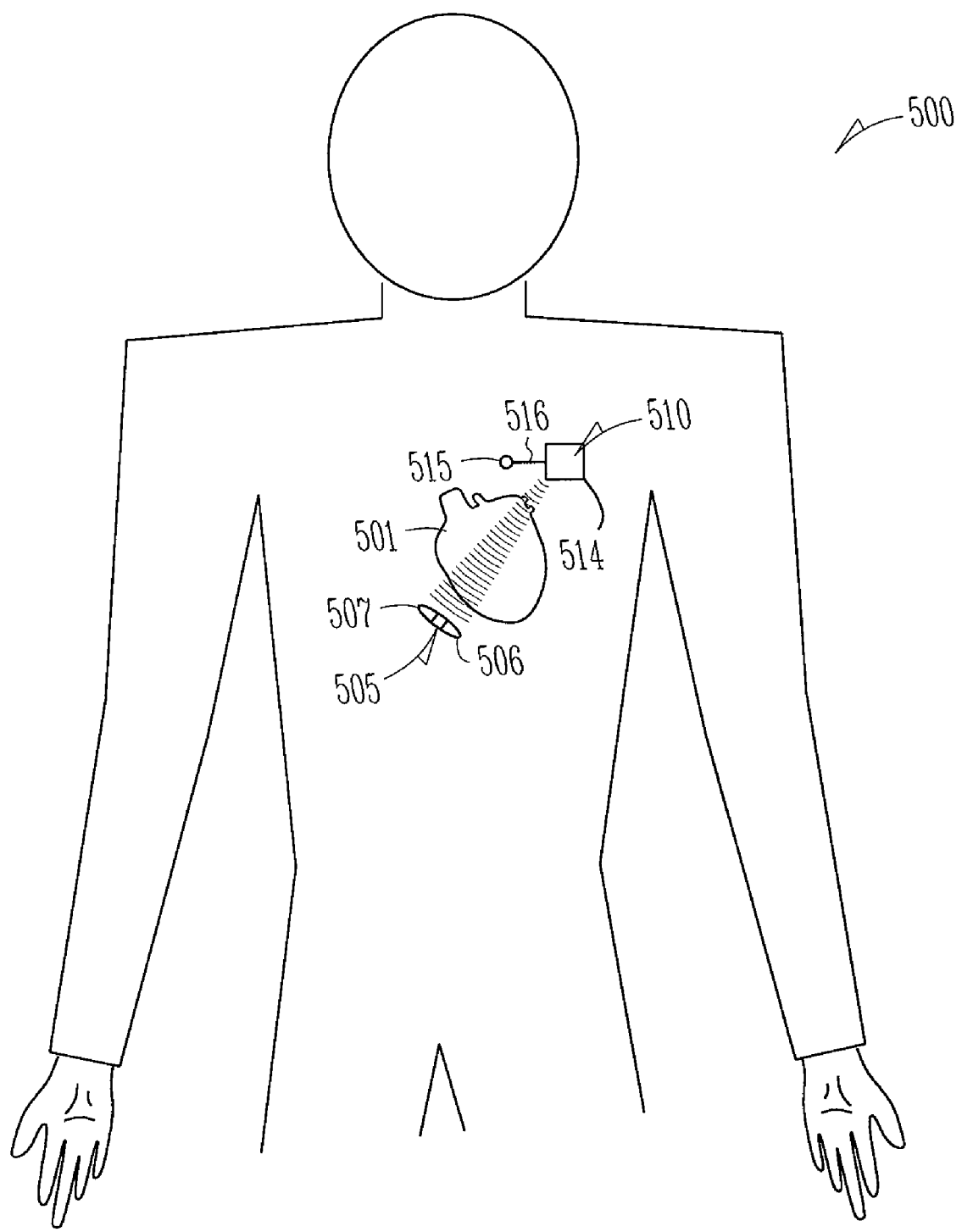
FIG. 5A is an illustration of a modular antitachyarrhythmia system that includes a therapy module and two sensing/analysis modules.

Another example of a modular antitachyarrhythmia therapy system is shown in FIG. 5A. The example system 500 includes a therapy module 505 and a separate sensing/analysis module 510 that performs sensing and analysis. Sensing/analysis module 510 includes a sensor 515 that detects a physiologic parameter and also includes controller circuitry that receives information from the sensor 515 and processes the information to determine whether a tachyarrhythmia is present and, if so, determines an appropriate antitachyarrhythmia therapy. In an example, the controller circuitry is contained in a housing 514 and the sensor 515 is connected to the housing with a lead 516. Analysis module 510 directs therapy module 505 to deliver an antitachyarrhythmia therapy through electrodes 506, 507. In an example, therapy module 505 delivers an antitachyarrhythmia therapy from electrode 506 through a portion of the heart 501 to electrode 507. In an example, antitachyarrhythmia therapy module 505 is implanted outside the heart as shown in FIG. 5A, such as in the subcutaneously below or between the ribs. In another example, antitachyarrhythmia module 505 is implanted in the heart, such as in the right atrium or right ventricle.

Figure 5B:
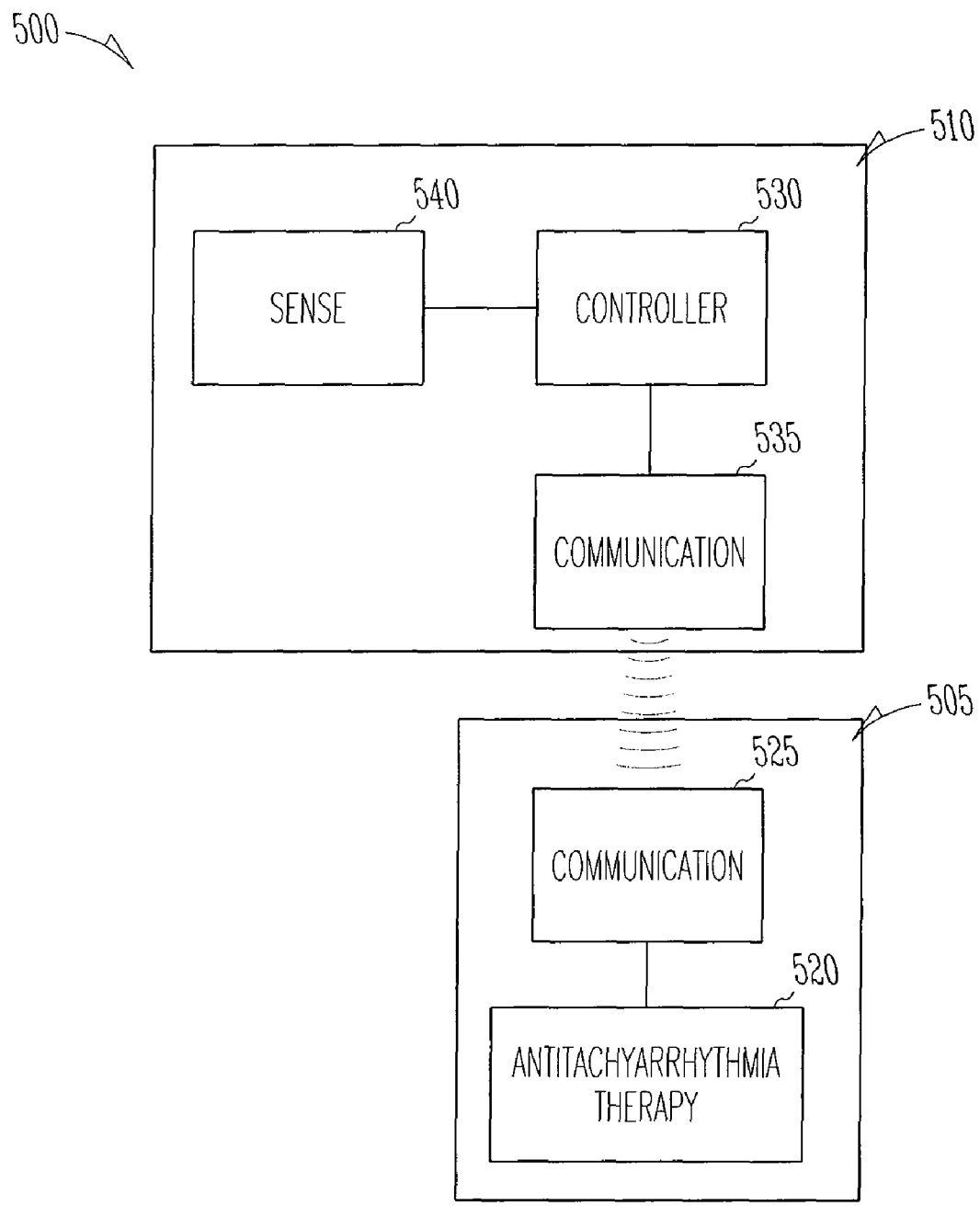
FIG. 5B is a schematic illustration of the system shown in FIG. 5A.

FIG. 5B shows a schematic illustration of the system illustrated in FIG. 5A. Sensing/analysis module 510 includes controller circuit 530, sensor circuit 540, and communication circuit 535. Sensor circuit 540 includes the sensor 515 that detects one or more physiological parameters. Controller circuit 530 analyzes physiological data provided by the sensor circuit 540 and determines whether a tachyarrhythmia is present and, if so, determines an appropriate antitachyarrhythmia therapy, such as a defibrillation shock therapy or antitachyarrhythmia pacing (ATP) therapy. A direction, such as a direction to initiate or adjust the antitachyarrhythmia therapy, is sent to the antitachyarrhythmia therapy module 505 through the communication circuit 535. In one example, the communication circuit 535 includes telemetry circuitry, such as an inductive or RF transmitter. In another example, the communication circuit 535 includes an inductive or RF transceiver. Antitachyarrhythmia therapy module 505 includes a communication circuit 525 that receives the communication from the communication circuit 535 in the analysis module 510. Antitachyarrhythmia therapy module 505 also includes an antitachyarrhythmia therapy circuit 520, which includes the electrodes 506, 507 shown in FIG. 5A. Antitachyarrhythmia therapy circuit 520 delivers the antitachyarrhythmia therapy determined by the controller circuit 530 through the electrodes 506, 507.

Figure 6A:
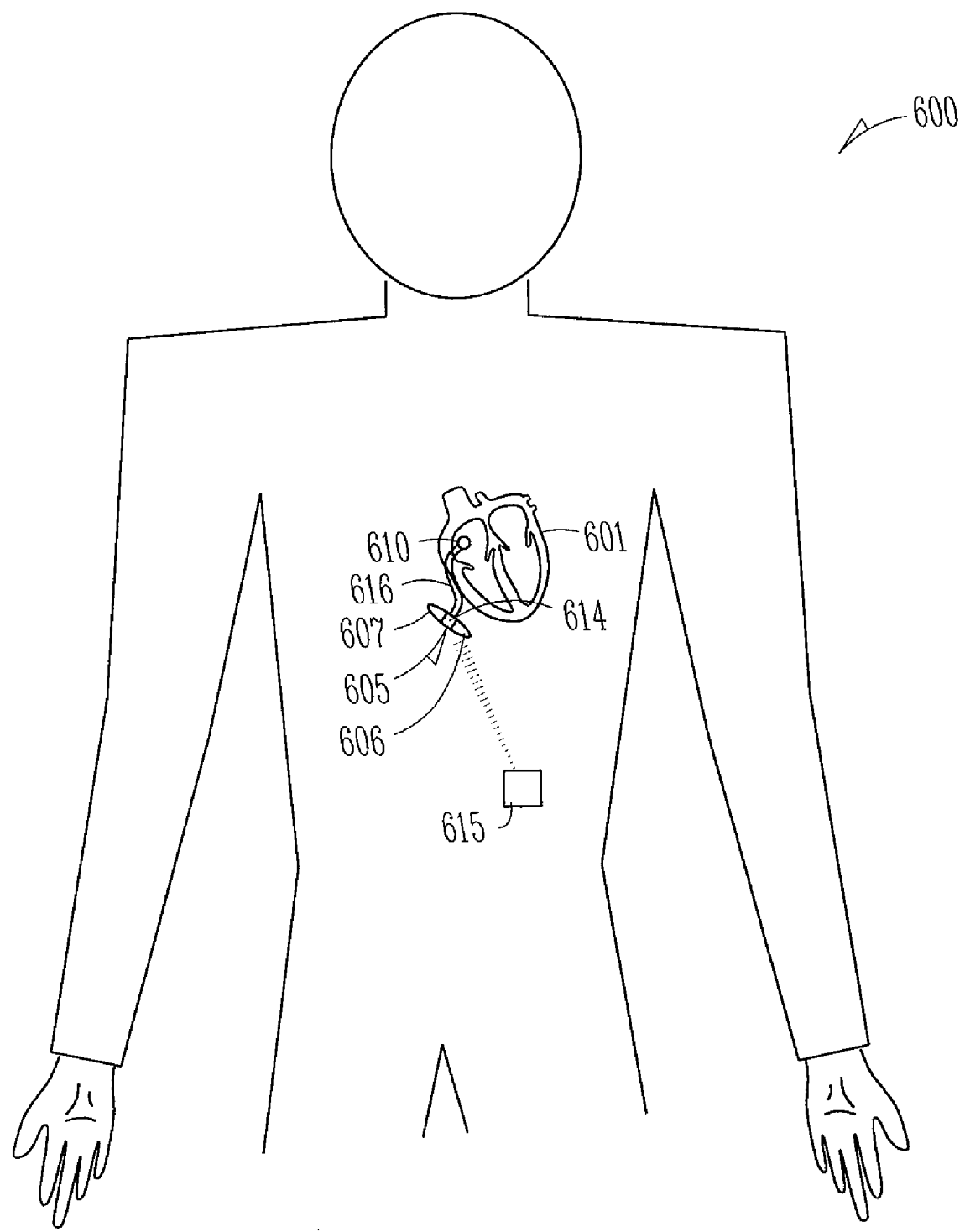
FIG. 6A is an illustration of a modular antitachyarrhythmia system that includes a sensing/therapy module and an analysis module.

Another example of a modular antitachyarrhythmia therapy system is shown in FIG. 6A. The example system 600 includes a sensing/therapy module 605 and a separate analysis module 615. Sensing/therapy module 605 includes a sensor 610 that detects a physiologic parameter and also includes therapy circuitry that delivers an antitachyarrhythmia therapy. In an example, sensor 610 is located in the heart. In another example, sensor 610 is located outside the heart. In an example, the therapy circuitry is contained in a housing 614 and the sensor 610 is connected to the housing with a lead 616. The sensing/therapy module 605 communicates wirelessly with an analysis module 615. Analysis module determines whether a tachyarrhythmia is present and, if so, directs sensing/therapy module 605 to deliver an appropriate antitachyarrhythmia therapy through electrodes 606, 607. In an example, therapy module 605 delivers an antitachyarrhythmia therapy from electrode 606 through a portion of the heart 601 to electrode 607. In an example, the sensing/therapy module 605 is implanted outside the heart, as shown in FIG. 6A. In another example, the sensing/therapy module is implanted in the heart.

Figure 6B:
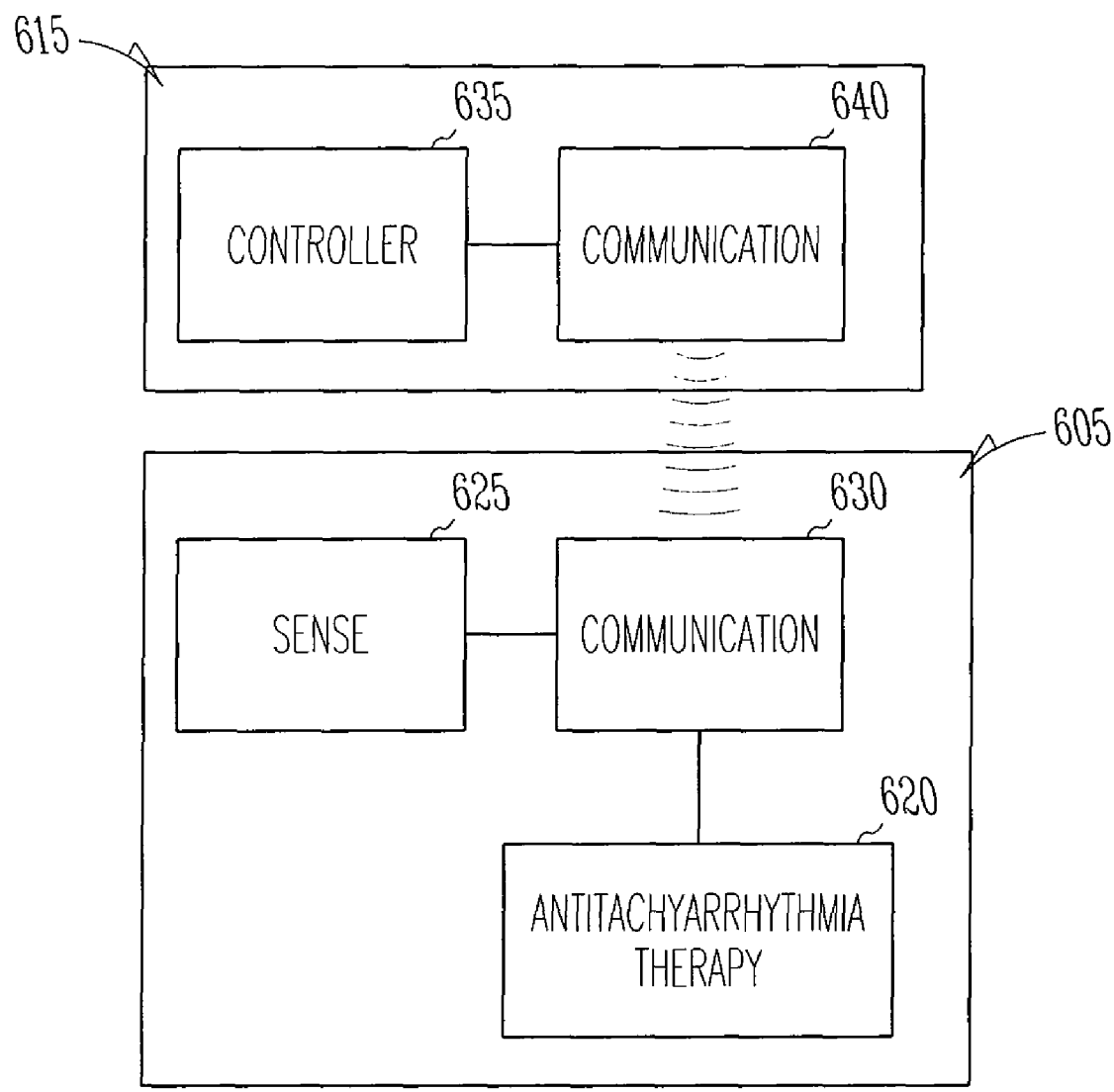
FIG. 6B is a schematic illustration of the system shown in FIG. 6A.

FIG. 6B shows a schematic illustration of the system illustrated in FIG. 6A. Sensing/therapy module 605 includes sense circuit 625, antitachyarrhythmia therapy circuit 620, and communication circuit 630. The antitachyarrhythmia therapy circuit 620 includes the electrodes 606, 607 shown in FIG. 6A. Sense circuit 625 includes the sensor 610 that detects one or more physiological parameters. Sensing/therapy module 605 sends physiological data through communication circuit 630 to the analysis module. Analysis module 615 includes a controller circuit 635 and a communication circuit 640. Communication circuit 640 receives the communication from the sensing/analysis module 605. In one example, the communication circuits 630, 640 each include an RF transceiver and the circuits communicate through RF signals. Controller circuit 635 analyzes physiological data provided by the sense circuit 640 and determines an antitachyarrhythmia therapy, such as a defibrillation shock therapy or ATP therapy. Analysis module then sends an antitachyarrhythmia therapy instruction through the communication circuit 640 to the antitachyarrhythmia therapy module 605. Antitachyarrhythmia therapy circuit 620 delivers the antitachyarrhythmia therapy determined by the controller circuit 635 through the electrodes 606, 607.

Figure 7A:
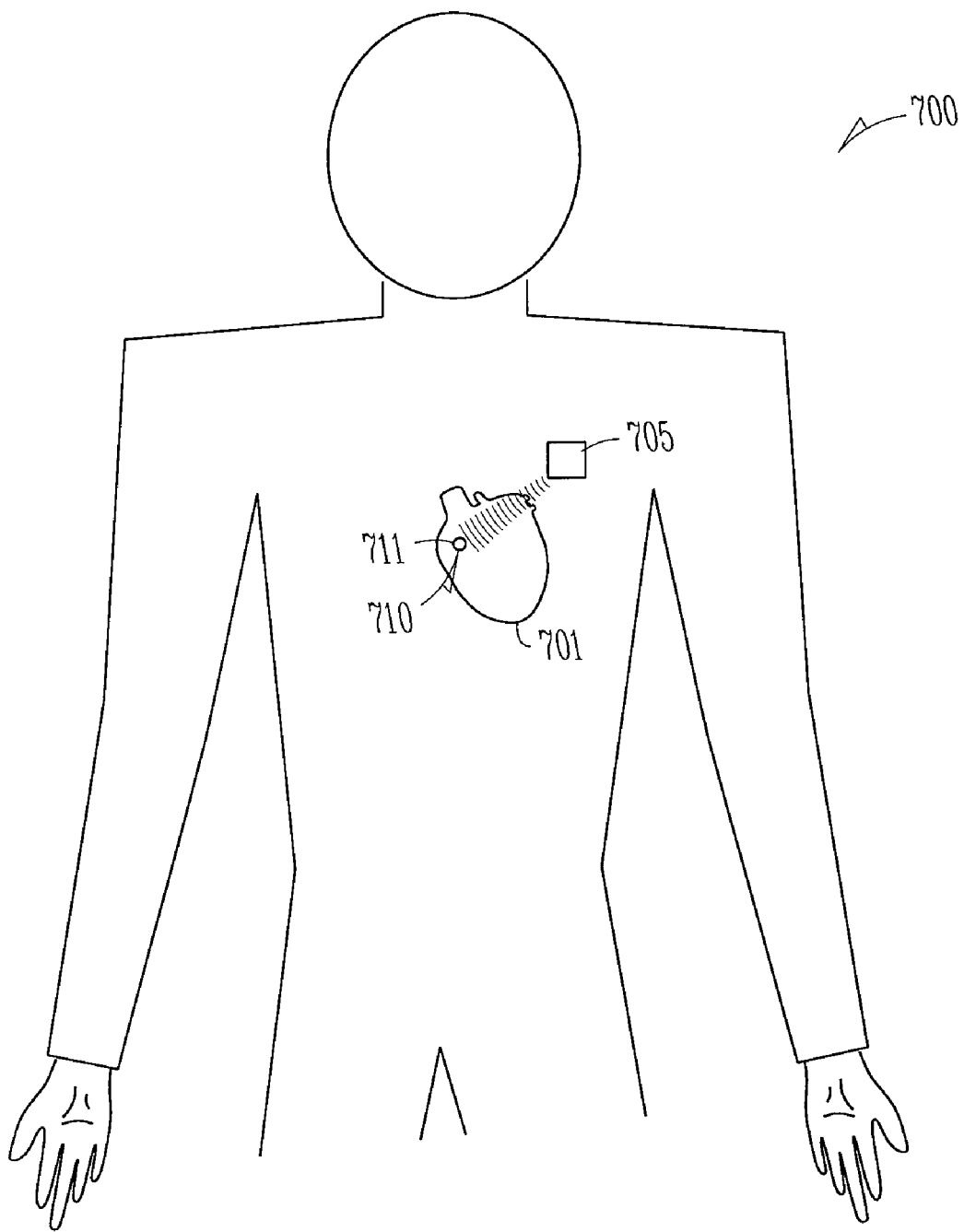
FIG. 7A is an illustration of a modular antitachyarrhythmia system that includes a sensing module and an analysis/therapy module.

Another example of a modular antitachyarrhythmia therapy system is shown in FIG. 7A. The example system 700 includes a sensing module 710 and an analysis/therapy module 705. Sensing module 710 includes a sensor 711 that detects a physiologic parameter. The sensing module 710 communicates wirelessly with an analysis/therapy module 715. Analysis/therapy module 705 includes controller circuitry that analyzes data provided by the sensing module 710 and determines whether a tachyarrhythmia is present and, if so, determines an appropriate antitachyarrhythmia therapy. Analysis/therapy module 705 also includes therapy circuitry that delivers the antitachyarrhythmia therapy, for example, to a heart 701.

Figure 7B:
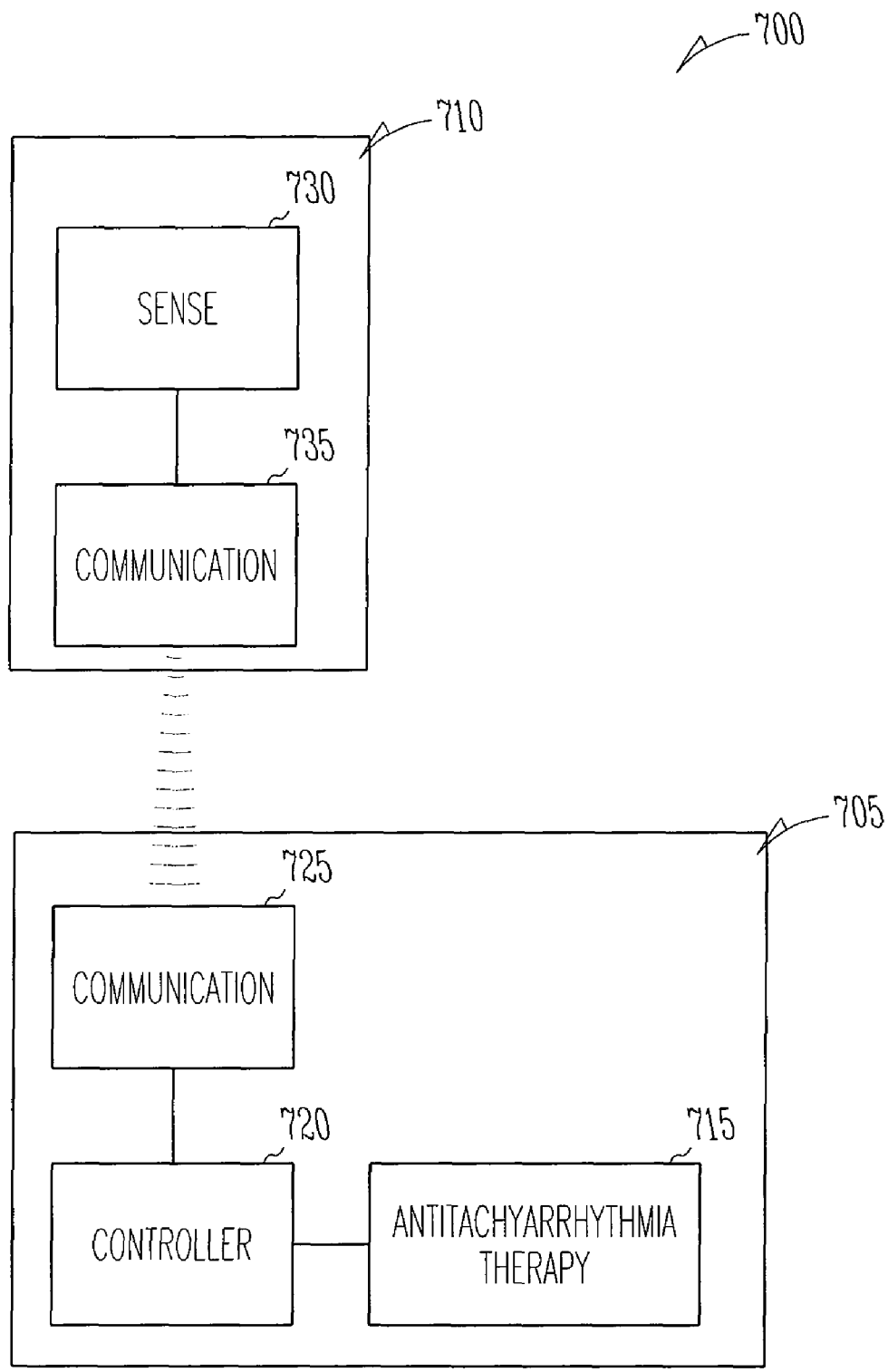
FIG. 7B is a schematic illustration of the system shown in FIG. 7A.

FIG. 7B shows a schematic illustration of the system illustrated in FIG. 7A. Sensing module 710 includes a sense circuit 730 that includes the sensor 711 shown in FIG. 7A. Sensing module 710 also includes a communication circuit 735 that sends information about sensed physiologic parameters to the analysis/therapy module 705. Analysis/therapy module 705 includes controller circuit 720, antitachyarrhythmia therapy circuit 715, and communication circuit 725. Communication circuit 725 receives the communication from the sensing module 710. In one example, the communication circuits 725, 735 each include telemetry circuitry, and the circuits communicate through RF or inductive signals. Controller circuit 720 analyzes physiological data provided by the sense circuit 730 and determines whether a tachyarrhythmia is present and, if so, determines an appropriate antitachyarrhythmia therapy, such as a defibrillation shock therapy or ATP therapy. The controller circuit 720 then sends an antitachyarrhythmia therapy delivery instruction to the antitachyarrhythmia therapy circuit 715. Antitachyarrhythmia therapy circuit 715 delivers the antitachyarrhythmia therapy determined by the controller circuit 720. In an example, the antitachyarrhythmia therapy circuit includes electrodes that are integrated into a housing of the analysis/therapy module that carries its electronics.

In other examples, one of the systems shown in FIGS. 1A-7A includes one or more additional modules. In one example, a system includes a memory module including a memory circuit and communication circuit. In another example, a system includes a pacing module including pacing circuitry. In another example, a system includes a respiratory sensing module including respiratory sensing circuitry. In another example, a system includes a respiratory stimulation module including respiratory stimulation circuitry. In another example, a system includes a chemical sensor module or a chemical or drug delivery module. In an example, a system includes sensors that detect blood chemistry in the heart or in arteries or other vessels. In an example, a system includes one or more sensors detect oxygen saturation and/or pH levels in blood.

In some examples, certain modules are combined into a system that includes at least two separately located modules that wirelessly communicate with each other. In an example, pacing circuitry is included in a defibrillation module or a heart sensing module. In another example, respiration sensing and respiration stimulation are performed by a single module. In another example, chemical sensors or chemical delivery mechanisms are included with antitachyarrhythmia therapy modules or other modules.

Figure 8A:
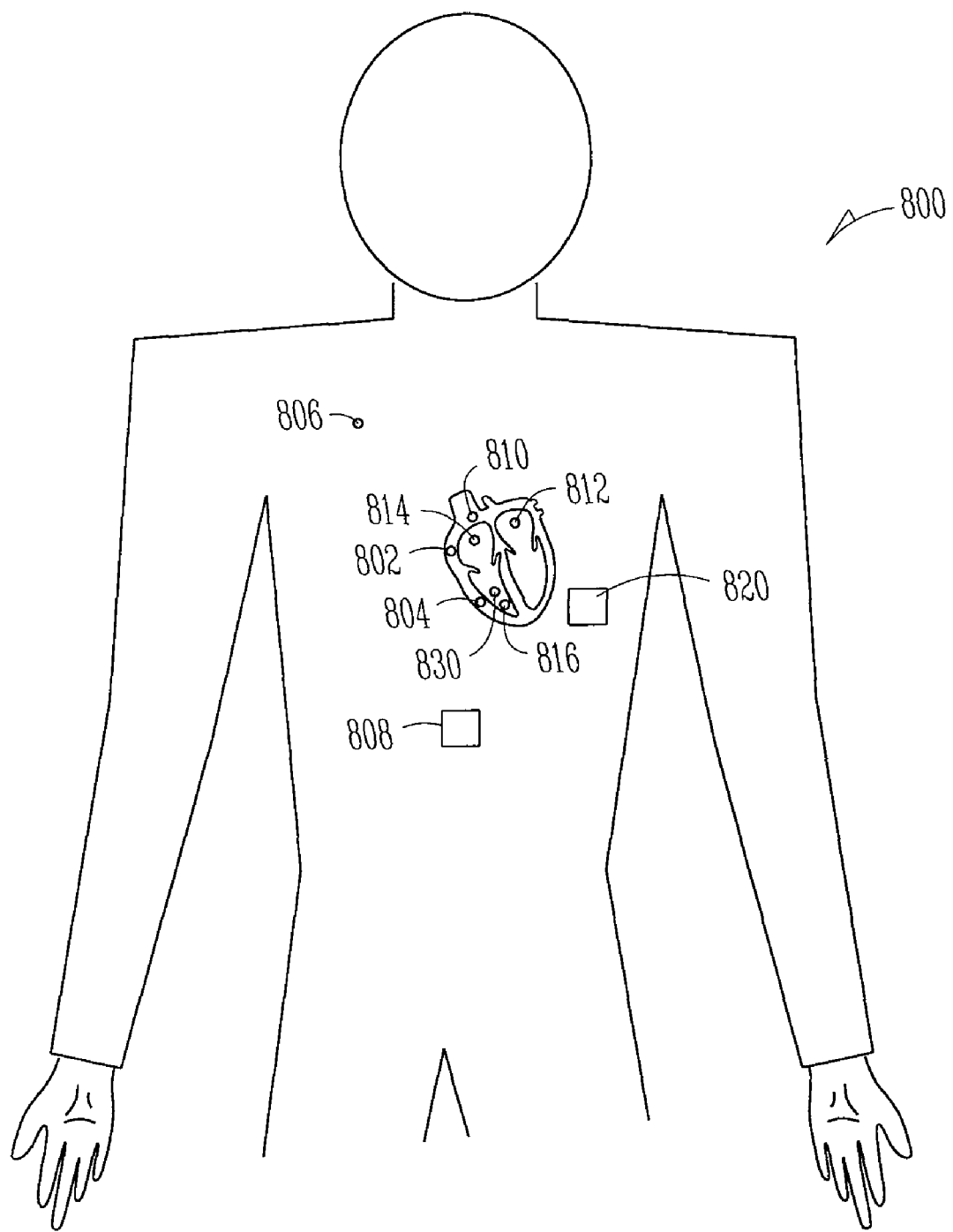
FIG. 8A is an illustration of a system that includes a plurality of sensing modules.

FIG. 8A shows an example of a modular implantable system 800 that includes a variety of separate sensor modules. FIG. 8B is a schematic illustration of the system shown in FIG. 8A that shows schematic illustrations of circuits in the modules. The system 800 includes separate modules 802, 804, 806, 812, 814, 816. In an example, each of the separate modules 802, 804, 806, 812, 814, 816 includes a sensor to sense a physiologic parameter and a wireless transmitter circuit to send a wireless communication that includes information about the physiologic parameter. In another example, two or more of the sense circuits are coupled to another module with a lead or are combined in a single module. In one example, module 802 includes a sense amplification circuit 842 (shown in FIG. 8B) to detect an intrinsic electrical heart signal and a wireless transmitter circuit 843 that transmits information about the intrinsic electrical heart signal. In one example, module 804 includes a heart sound sensor 844 to detect a heart sound and a wireless transmitter circuit 845 that transmits information about the heart sound. In one example, module 806 includes a respiration sensor 846 and a wireless transmitter circuit 847 that transmits information about the respiration. In one example, module 808 includes a wireless receiver circuit 849 to receive a diaphragmatic pacing instruction and a diaphragm stimulation circuit 848 to deliver a diaphragmatic pacing pulse. In an alternative example, module 806 and 808 are combined in a single module.

In one example, module 810 includes a pacing stimulation circuit 850 to deliver a pacing pulse and a wireless receiver circuit 851 that receive a pacing instruction. In this example, module 812 includes a blood pressure sensor 852 to detect blood pressure and a wireless transmitter circuit 853 that transmits information about the blood pressure. In an example, module 812 is sized and shaped for implantation in the heart, or in vasculature near the heart. In another example, module 812 is sized and shaped for implantation in pulmonary vasculature, such as in the pulmonary vascular bed. In an example system, the pacing stimulation circuit in module 810 adjusts delivery of a pacing pulse in response to information provided from another module, such as information about the blood pressure provided by module 812. In one example, module 814 includes an atrial sensing circuit 854 that senses an intrinsic electrical atrial signal and a wireless communication circuit 855 that transmits information includes information about the atrial signal. In one example, module 816 includes a ventricular sensing circuit 856 that senses an intrinsic electrical ventricular signal, and a wireless transmitter 857 that transmits information about the ventricular signal. In some examples, one or more of modules 802, 804, 806, 812, 814, 816, include circuitry that processes a signal or data obtained from a physiological sensor.

In one example, module 820 includes a wireless receiver or transceiver circuit 821 that receives a wireless communication from one or more of the other modules. Module 820 also includes a controller circuit 822 that uses the information about one or more physiologic parameters received from one or more of the other modules 802, 804, 806, 812, 814, 816, such as to provide diagnostic information or to determine therapy. In an example, the controller circuit 822 uses information about the atrial signal received from module 814. In another example, the controller circuit 822 uses information about the ventricular signal received from module 816. In another example, the controller circuit 822 uses information about both the atrial and ventricular signals. In an example, module 820 also includes an antitachyarrhythmia therapy circuit that delivers a responsive antitachyarrhythmia therapy. In another example, module 820 includes a wireless transmitter circuit 821 that transmits a wireless antitachyarrhythmia therapy instruction to module 830, which includes a communication circuit 834 and antitachyarrhythmia circuitry 832 that delivers an antitachyarrhythmia therapy in accordance with the instruction from module 820. In an example, modules 820 and 830 each include an antitachyarrhythmia therapy circuit. In an example, module 820 is implanted subcutaneously and can be replaced without replacing other modules.

In another example, some of the modules 802, 804, 806, 808, 810, 812, 814, 816, 820, 830 are combined together in a system that includes at least two separate modules that wirelessly communicate with each other. In an example, the modules 802, 804, 812 that respectively sense blood pressure, heart sound, and an intrinsic electrical heart signal are combined into a single module 803 that includes such sensors and a wireless transmitter that transmits information about various physiological parameters detected by the sensors.

In an example, the system receives information about physiologic parameters through multiple channels. In one example, the system 800 is senses at least two physiologic parameters concurrently using physically separate modules, and includes a memory circuit that records information relating to the at least two physiologic parameters. In an example, the system includes stores information about physiologic parameters received before a tachyarrhythmia in the memory circuit. In an example, the system includes an implantable memory circuit that can be replaced without replacing other modules.

Figure 9:
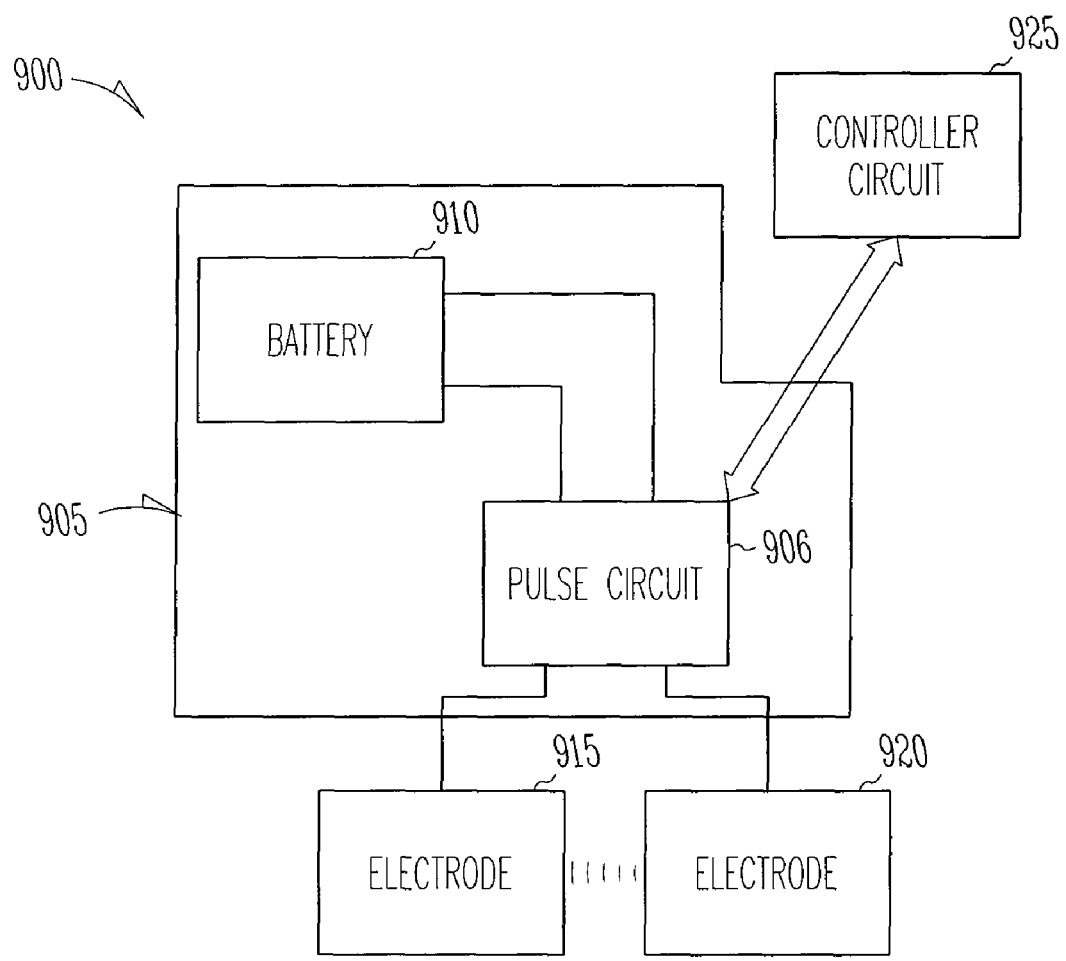
FIG. 9 is a schematic illustration of an embodiment of an antitachyarrhythmia therapy circuit.

FIG. 9 is a schematic illustration of an example of an antitachyarrhythmia therapy circuit 900. A pulse generator 905 includes a battery 910 and a pulse circuit 906. In an example, the pulse circuit 906 includes a capacitor for building a charge that is deliverable in a pulse across the electrodes. The pulse generator 905 receives an instruction from a controller circuit 925. In an example, the controller circuit 925 communicates through telemetry circuitry coupled to the pulse generator 905. In another example, the controller circuit 925 is physically connected to the pulse generator 905. The controller circuit 925 instructs the pulse generator 905 to draws power from the battery and delivers an energy, such as a defibrillation shock, across electrodes 915, 920.

It is to be understood that the above description is intended to be illustrative, and not restrictive. Since many embodiments of the invention can be made without departing from the spirit and scope of the invention, the invention resides in the claims hereinafter appended.

What is claimed is:

1. A modular implantable device comprising: an implantable first defibrillation circuit module configured to deliver a first defibrillation shock; an implantable second defibrillation Circuit module, physically separate from the first defibrillation circuit module, configured to deliver a second defibrillation shock coordinated with the first defibrillation shock; and a controller circuit configured to direct coordinated delivery of the first and second defibrillation shocks; and a first sensing circuit, physically separate from the first defibrillation circuit module and the second defibrillation circuit module, the first sensing circuit including a sensor configured to sense a physiologic parameter and a wireless transmitter circuit to send a wireless communication to the controller circuit, and wherein the first sensing circuit is shaped and configured to be implanted within at least one of the heart, or the vasculature, wherein said device further comprises an implantable third circuit, separate from the first and second circuit, the third circuit including a diaphragm stimulation circuit to deliver a diaphragmatic pacing pulse.

2. The modular implantable device of claim 1, wherein the controller circuit is wirelessly communicatively coupled to at least one of the first and second defibrillation circuit modules.

3. The modular implantable device of claim 1, wherein the controller circuit is shaped and configured to be implanted subcutaneously and to be explanted without explanting the first defibrillation circuit and second defibrillation circuit.

4. The modular implantable device of claim 1, wherein the controller circuit is configured to analyze the information derived from the physiologic parameter received from the first sensing circuit to determine a therapy.

5. The modular implantable device of claim 1, wherein the first sensing circuit includes a sense amplification circuit to detect an intrinsic electrical heart signal and wherein the wireless communication includes information derived from the intrinsic electrical heart signal.

6. The modular implantable device of claim 1, wherein the first sensing circuit includes a heart sound sensor to detect a heart sound and wherein the wireless communication includes information derived from the heart sound.

7. The modular implantable device of claim 1, wherein the first sensing circuit includes a respiration sensor to measure respiration and the wireless communication includes information derived from the respiration.

8. The modular implantable device of claim 1, further comprising an implantable third circuit, separate from the first and second defibrillation circuits, the third circuit including a pacing stimulation circuit to deliver a pacing pulse.

9. The modular implantable device of claim 8, wherein the first sensing circuit provides a blood pressure sensor to detect blood pressure and the wireless communication includes information derived from the blood pressure, and the pacing stimulation circuit is configured to adjust delivery of the pacing pulse in response to the information derived from the blood pressure.

10. The modular implantable device of claim 8, wherein the third circuit is physically located separate from the first sensing circuit but electrically connected to the first sensing circuit.

11. The modular implantable device of claim 1, wherein:
the first sensing circuit includes an atrial sensing circuit to sense an intrinsic electrical atrial signal and the wireless communication includes information derived from the atrial signal,
the modular implantable device further comprises a ventricular sensing circuit to sense an intrinsic electrical ventricular signal and send a wireless communication that includes information derived from the ventricular signal; and
the controller circuit is configured to analyze the information derived from at least one of the atrial signal and the ventricular signal to determine therapy.

12. The modular implantable device of claim 1, wherein the first sensing circuit is shaped and configured to be implanted in the heart.

13. The modular implantable device of claim 1, wherein the first sensing circuit is shaped and configured to be implanted in a pulmonary vessel.

14. The modular implantable device of claim 1, wherein the first sensing circuit is shaped and configured to be implanted in a peripheral cardiac vessel.

15. The modular implantable device of claim 1, wherein the first sensing circuit is configured to send the wireless communication as an electrical signal through a human or animal body, wherein the body is used as a conductive medium for the wireless communication.

16. The modular implantable device of claim 1, wherein the modular device is configured to sense at least two physiologic parameters concurrently, and further includes a memory circuit configured to record information relating to the at least two physiologic parameters.

17. The modular implantable device of claim 1, further including an implantable memory circuit that is configured to be replaced without requiring replacement of the first or second defibrillation circuit modules, the controller circuit, or the first sensor circuit.

18. The modular implantable device of claim 1, wherein the first sensing circuit provides a blood pressure sensor to detect blood pressure and the wireless communication includes information derived from the blood pressure.

* * * * *